(12) United States Patent
Harms et al.

(10) Patent No.: US 10,286,158 B2
(45) Date of Patent: *May 14, 2019

(54) MEDICATION DELIVERY DEVICE

(71) Applicant: Sanofi-Aventis Deutschland GmbH, Frankfurt am Main (DE)

(72) Inventors: Michael Harms, Oberursel (DE); Steffen Raab, Frankfurt am Main (DE); Dominic George Webber, Cambridge (GB); James Roberts Howarth, Cambridge (GB); Trevor John Beckett, Cambridge (GB); Geoffrey Philip Gray, Herts (GB); John David Cross, Northampton (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 135 days.

This patent is subject to a terminal disclaimer.

(21) Appl. No.: 15/175,406

(22) Filed: Jun. 7, 2016

(65) Prior Publication Data

US 2016/0310669 A1 Oct. 27, 2016

Related U.S. Application Data

(63) Continuation of application No. 14/049,916, filed on Oct. 9, 2013, now Pat. No. 9,802,003, which is a (Continued)

(30) Foreign Application Priority Data

May 2, 2008 (EP) ..................................... 08008353

(51) Int. Cl.
| | |
|---|---|
| *A61M 5/31* | (2006.01) |
| *A61M 5/315* | (2006.01) |
| *A61M 5/24* | (2006.01) |

(52) U.S. Cl.
CPC .......... *A61M 5/31576* (2013.01); *A61M 5/24* (2013.01); *A61M 5/3155* (2013.01); (Continued)

(58) Field of Classification Search
CPC .. A61M 2005/2407; A61M 2005/2488; A61M 2202/04; A61M 2205/581; (Continued)

(56) References Cited

U.S. PATENT DOCUMENTS

| | | |
|---|---|---|
| 533,575 A | 2/1895 | Wilkens |
| 4,568,335 A | 2/1986 | Updike et al. |

(Continued)

FOREIGN PATENT DOCUMENTS

| | | |
|---|---|---|
| CA | 2138528 | 12/1998 |
| CA | 2359375 A1 | 7/2000 |

(Continued)

OTHER PUBLICATIONS

HumaPen Ergo Customer Manual dated Aug. 15, 2000.
(Continued)

*Primary Examiner* — Imani N Hayman
(74) *Attorney, Agent, or Firm* — Fish & Richardson P.C.

(57) ABSTRACT

A medication delivery device and/or dosing mechanisms suitable for use in medication delivery devices, in particular in pen-type injectors, preferably having a dose setting system and a drive device enabling the administration of a medicinal product from a single- or multi-dose medication cartridge.

31 Claims, 7 Drawing Sheets

Related U.S. Application Data continuation of application No. 13/416,685, filed on Mar. 9, 2012, now Pat. No. 8,579,867, which is a continuation of application No. 12/194,705, filed on Aug. 20, 2008, now Pat. No. 8,187,233.

(52) U.S. Cl.
CPC .... *A61M 5/31511* (2013.01); *A61M 5/31533* (2013.01); *A61M 5/31535* (2013.01); *A61M 5/31541* (2013.01); *A61M 5/31543* (2013.01); *A61M 5/31551* (2013.01); *A61M 5/31583* (2013.01); *A61M 5/31585* (2013.01); *A61M 5/31593* (2013.01); *A61M 5/3146* (2013.01); *A61M 5/31558* (2013.01); *A61M 5/31575* (2013.01); *A61M 2005/2407* (2013.01); *A61M 2005/2488* (2013.01); *A61M 2202/04* (2013.01); *A61M 2205/581* (2013.01); *A61M 2205/582* (2013.01); *A61M 2207/00* (2013.01)

(58) Field of Classification Search
CPC ........ A61M 2205/582; A61M 2207/00; A61M 5/24; A61M 5/3146; A61M 5/31511; A61M 5/31533; A61M 5/31535; A61M 5/31541; A61M 5/31543; A61M 5/3155; A61M 5/31551; A61M 5/31558; A61M 5/31575; A61M 5/31576; A61M 5/31583; A61M 5/31585; A61M 5/31593
See application file for complete search history.

(56) References Cited

U.S. PATENT DOCUMENTS

| | | |
|---|---|---|
| 4,865,591 A | 9/1989 | Sams |
| 5,092,842 A | 3/1992 | Bechtold et al. |
| 5,226,895 A | 7/1993 | Harris |
| 5,226,896 A | 7/1993 | Harris |
| 5,279,586 A | 1/1994 | Balkwill |
| 5,304,152 A | 4/1994 | Sams |
| 5,320,609 A | 6/1994 | Haber et al. |
| 5,378,233 A | 1/1995 | Haber et al. |
| 5,383,865 A | 1/1995 | Michel |
| 5,391,157 A | 2/1995 | Harris et al. |
| 5,480,387 A | 1/1996 | Gabriel et al. |
| 5,505,704 A | 4/1996 | Pawelka et al. |
| 5,582,598 A | 12/1996 | Chanoch |
| 5,599,314 A | 2/1997 | Neill |
| 5,611,783 A | 3/1997 | Mikkelsen |
| 5,626,566 A | 5/1997 | Petersen et al. |
| 5,674,204 A | 10/1997 | Chanoch |
| 5,688,251 A | 11/1997 | Chanoch |
| 5,743,889 A | 4/1998 | Sams |
| 5,807,346 A | 9/1998 | Frezza |
| 5,820,602 A | 10/1998 | Kovelman et al. |
| 5,827,232 A | 10/1998 | Chanoch et al. |
| 5,851,079 A | 12/1998 | Horstman et al. |
| 5,921,966 A | 7/1999 | Bendek et al. |
| 5,957,896 A | 9/1999 | Bendek et al. |
| 5,961,495 A | 10/1999 | Walters et al. |
| 5,984,900 A | 11/1999 | Mikkelsen |
| 6,004,297 A | 12/1999 | Steenfeldt-Jensen et al. |
| 6,193,698 B1 | 2/2001 | Kirchhofer et al. |
| 6,221,046 B1 | 4/2001 | Burroughs et al. |
| 6,235,004 B1 | 5/2001 | Steenfeldt-Jensen et al. |
| 6,248,095 B1 | 6/2001 | Giambattista et al. |
| 6,562,006 B1 | 5/2003 | Hjertman et al. |
| 6,613,023 B2 | 9/2003 | Kirchhofer et al. |
| 6,699,224 B2 | 3/2004 | Kirchhofer et al. |
| 6,899,698 B2 | 5/2005 | Sams |
| 6,932,794 B2 | 8/2005 | Giambattista et al. |
| 6,936,032 B1 | 8/2005 | Bush, Jr. et al. |
| 7,169,132 B2 | 1/2007 | Bendek et al. |
| 7,241,278 B2 | 7/2007 | Moller |
| 7,678,084 B2 | 3/2010 | Judson et al. |
| 7,740,618 B2 | 6/2010 | Markussen |
| 7,850,662 B2 | 12/2010 | Veasey et al. |
| 8,186,233 B2 | 5/2012 | Joung et al. |
| 8,187,233 B2 | 5/2012 | Harms et al. |
| 8,267,900 B2 | 9/2012 | Harms et al. |
| 8,491,538 B2 | 7/2013 | Kohlbrenner et al. |
| 8,579,867 B2 | 11/2013 | Harms et al. |
| 8,647,309 B2 | 2/2014 | Harms et al. |
| 8,707,727 B2 | 4/2014 | Hasturk et al. |
| 8,992,487 B2 | 3/2015 | Eich et al. |
| 9,526,844 B2 | 12/2016 | Veasey et al. |
| 9,802,003 B2 | 10/2017 | Harms et al. |
| 2002/0052578 A1 | 5/2002 | Moller |
| 2002/0120235 A1 | 8/2002 | Enggaard |
| 2003/0050609 A1 | 3/2003 | Sams |
| 2004/0003297 A1 | 1/2004 | Ma |
| 2004/0059299 A1 | 3/2004 | Moller |
| 2004/0097883 A1 | 5/2004 | Roe |
| 2004/0210199 A1 | 10/2004 | Atterbury et al. |
| 2004/0267207 A1 | 12/2004 | Veasey et al. |
| 2004/0267208 A1 | 12/2004 | Veasey et al. |
| 2005/0055011 A1 | 3/2005 | Enggaard |
| 2005/0113765 A1 | 5/2005 | Veasey et al. |
| 2006/0153693 A1 | 7/2006 | Fiechter et al. |
| 2006/0178634 A1 | 8/2006 | Wyrick |
| 2007/0016143 A1 | 1/2007 | Miller et al. |
| 2009/0275916 A1 | 11/2009 | Harms et al. |

FOREIGN PATENT DOCUMENTS

| | | |
|---|---|---|
| CN | 101039713 A | 9/2007 |
| EP | 0496141 A1 | 7/1992 |
| EP | 0554995 A1 | 8/1993 |
| EP | 0554996 A1 | 8/1993 |
| EP | 0897728 A1 | 2/1999 |
| EP | 0897729 A2 | 2/1999 |
| EP | 0937471 A2 | 2/1999 |
| EP | 0937476 A2 | 8/1999 |
| EP | 1250167 B1 | 7/2005 |
| EP | 1728529 A1 | 12/2006 |
| EP | 1776975 A2 | 4/2007 |
| EP | 1974761 A2 | 10/2008 |
| EP | 2274029 B1 | 11/2011 |
| EP | 2274030 B1 | 9/2012 |
| TW | 445157 A4 | 7/2001 |
| TW | 200507897 | 3/2005 |
| TW | 200942284 A1 | 10/2009 |
| WO | 9307922 A1 | 4/1993 |
| WO | 9324160 A1 | 12/1993 |
| WO | 9710864 A1 | 3/1997 |
| WO | 9938544 A2 | 8/1999 |
| WO | 0110484 A1 | 2/2001 |
| WO | 0230495 A2 | 4/2002 |
| WO | 02092153 A2 | 11/2002 |
| WO | 03080160 A1 | 10/2003 |
| WO | 2004007003 A1 | 1/2004 |
| WO | 2004078239 A1 | 9/2004 |
| WO | 2006045529 A1 | 5/2006 |
| WO | 2006058883 A2 | 6/2006 |
| WO | 2006077466 A2 | 7/2006 |
| WO | 2006084876 A1 | 8/2006 |
| WO | 2006128794 A2 | 12/2006 |
| WO | 2007006662 A1 | 1/2007 |
| WO | 2007017052 A1 | 2/2007 |
| WO | 2007017053 A1 | 2/2007 |
| WO | 2008000827 A1 | 1/2008 |
| WO | 2008031235 A1 | 3/2008 |
| WO | 2008074897 | 6/2008 |

OTHER PUBLICATIONS

HumaPen Ergo Customer Letter Regarding Safety Reminder dated Dec. 11, 2001.
"Pen-injectors for medical use—Part 1: Pen-injectors—Requirements and test methods," International Standard, reference No. ISO 11608-1:2000(E), first edition Dec. 15, 2000.

MEDICATION DELIVERY DEVICE

CROSS REFERENCE TO RELATED APPLICATIONS

The present application is a continuation of U.S. patent application Ser. No. 14/094,916 filed Oct. 9, 2013 which is a continuation of U.S. patent application Ser. No. 13/416,685 filed Mar. 9, 2012 which is a continuation of U.S. patent application Ser. No. 12/194,705 filed Aug. 20, 2008.

The present invention relates to a medication delivery device, a use of the device and a method of manufacturing or assembling the device.

The invention refers particularly to dosing mechanisms suitable for use in medication delivery devices, in particular in pen-type injectors, preferably having dose setting means and a drive device enabling the administration of a medicinal product from a single- or multi-dose medication cartridge. In particular, the present invention relates to such medication delivery devices where a user may set a dose of medication to be delivered from a multi-dose cartridge. Most preferably, the medication delivery device comprises a single- or multi-dose medication cartridge which can be replaced when the medication has been fully dispensed.

The present invention further relates to a reset mechanism for a medication delivery device, and particularly to a reset mechanism comprising a reset element which is engaged with a piston rod of the medication delivery device. Most preferably the reset mechanism according to the preset invention is activated and deactivated by a medication receptacle being engaged with and disengaged from the housing of the medication delivery device, respectively.

Such medication delivery devices have application where regular injections by persons without formal medical training occur, i.e., patients. This is increasingly common amongst those having diabetes where self-treatment enables such persons to conduct effective management of their diabetes.

These circumstances set a number of requirements for medication delivery devices of this kind. The device must be robust in construction, yet easy to use in terms of the manipulation of the parts, understanding by a user of its operation and the delivery of the required dose of medicament. Dose setting must be easy and unambiguous. In the case of those with diabetes, many users will be physically infirm and may also have impaired vision requiring the dosing mechanism to have a drive device which requires a low dispensing force and the medication delivery device to have an easy to read dose setting display.

As a result of environmental and economical reasons this kind of medication delivery device has been developed to allow only a part of the device to be discarded after all the medicament has been delivered, usually the medication cartridge only. This provides the additional requirement for such a medication delivery device that the resetting of the drive mechanism, when a new cartridge is attached to or inserted into the medication delivery device, needs to be easy and unambiguous without the need for the user to touch any component of the drive mechanism directly, thereby reducing the possibility of damage to the drive mechanism through e.g. contamination.

A further requirement of such reusable devices is that when a new cartridge is attached there should be no movement of the bung in the cartridge and thus no pressurisation of the contents of the cartridge prior to dose setting and dose delivery. If this occurs, the accuracy of the device could be affected.

User operated medication delivery devices are well known within the medical field.

WO 2004/078239 A1 discloses a drive mechanism for a drug delivery device with a housing having a helical thread, a dose dial sleeve having a helical thread engaged with the helical thread of the housing, a drive sleeve releasably connected to the dose dial sleeve and a clutch means located between the dose dial sleeve and the drive sleeve. When the dose dial sleeve and the drive sleeve are coupled via the clutch means, both are allowed to rotate with respect to the housing. When the dose dial sleeve and the drive sleeve are decoupled, rotation of the dose dial sleeve with respect to the housing is allowed whilst rotation of the drive sleeve with respect to the housing is not allowed, whereby axial movement of the drive sleeve is allowed so that a force is transferred in the longitudinal direction to a piston rod for medication delivery. This document neither describes the replacement of the cartridge, nor a resetting of the drive mechanism.

The following prior art documents address the reusability of such devices using a disposable and replaceable medicament cartridge that is attachable to/detachable from a reusable (resettable) drive mechanism.

In EP 0 554 996 B1 discloses an injection device comprising a housing and means for mounting a fluid containing cartridge containing an internal piston to the housing. A lead screw is movably mounted within the housing and a dose setting means is provided for selecting the amount of fluid to be delivered by the device. This device provides a solution for changing the cartridge and resetting the dosing mechanism of the reusable injection device. The new cartridge is inserted into the housing which is then screwed into place while the piston of the cartridge pushes the lead screw into the device which may have the disadvantage of applying pressure to the piston at the end of the screwing.

U.S. Pat. No. 5,827,232 teaches a medication delivery pen, comprising a disposable medication containing cartridge assembly. The cartridge assembly comprises a cartridge with a pierceably sealed distal end and a plunger in sliding fluid tight engagement therein to dispense medication from the cartridge when the plunger slides in a distal direction. Furthermore, the medication delivery pen comprises a reusable pen body assembly which has a housing, a lead screw disposed in the housing and a driver means for moving the lead screw distally in the pen body assembly selected amounts. Whilst this device provides a solution for resetting a medication delivery pen drive mechanism it does require the user to align the cartridge holder with slots at the distal end of the piston rod which may be difficult for users with impaired eyesight and/or impaired dexterity.

WO 1997/010864 A1 describes a medication delivery pen comprising a cartridge holder assembly for holding a cartridge having a plunger, the cartridge holder assembly having a plurality of threads at a proximal end. A pen body assembly comprises a plurality of threads at a distal end for threading with the threads in the cartridge holder assembly. A lead screw extends form the distal end for engaging the plunger in the cartridge. Means for driving the lead screw into the cartridge are provided to move the plunger in the distal direction. Furthermore, means for disengaging the driving means from the lead screw are provided to permit the lead screw to automatically and easily retract into the pen body when the pen body assembly approaches and is being threaded to the cartridge holder assembly. However, the disclosed solution for mounting a new cartridge holder assembly to the reusable pen body assembly may have the disadvantage of applying pressure to the plunger at the end of the assembling.

The object of the invention is avoid the disadvantages of known medication delivery devices, particularly to provide a flexible reset mechanism for use in a medication delivery device by means of which the medication delivery device can be reset for re-use when the medication cartridge is replaced.

Figure 1A:
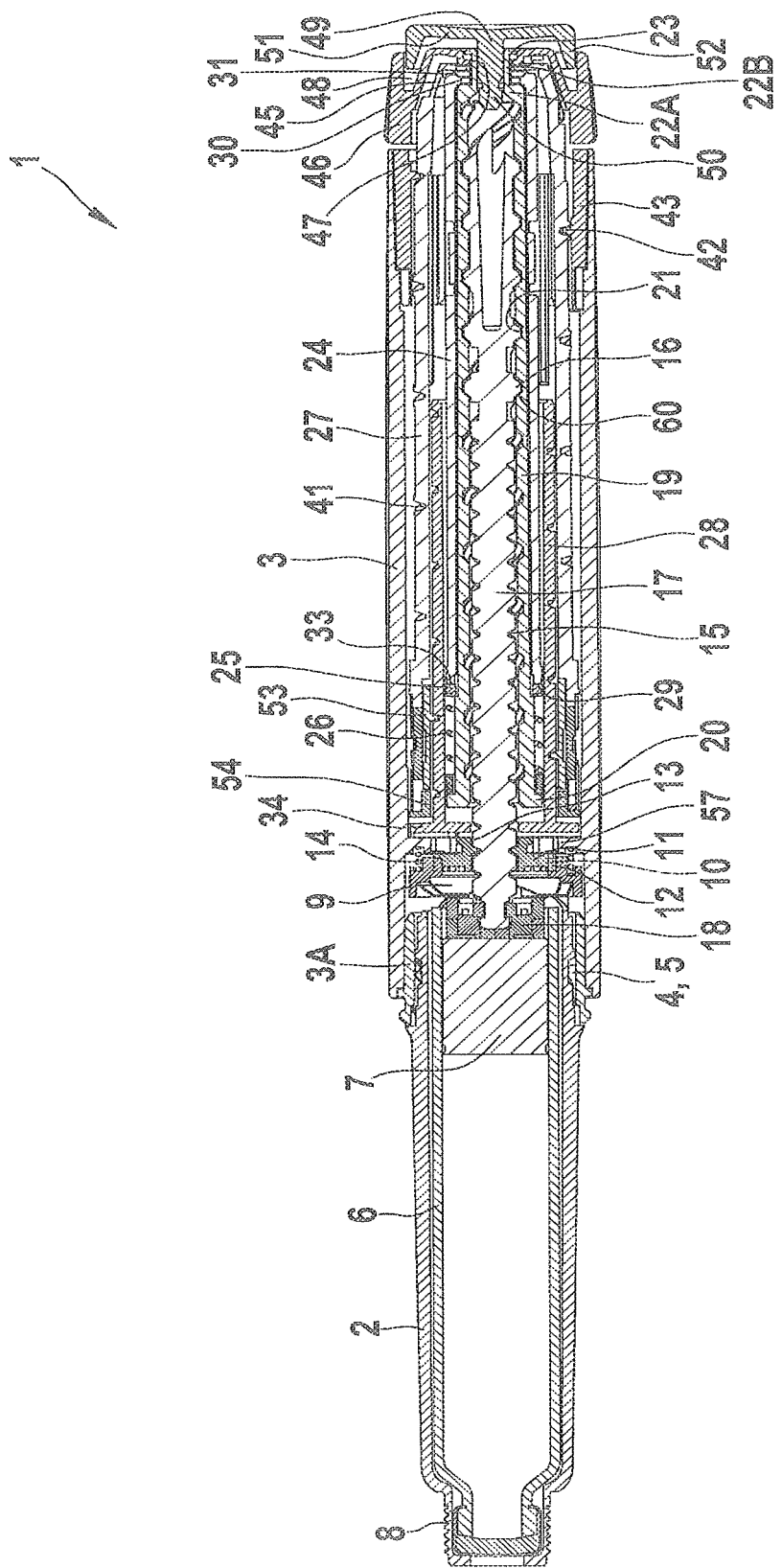
FIGS. 1a to 1c show a cross-sectional view of one embodiment of a medication delivery device according to the invention in three different states.

The medication delivery device according to the present invention provides a valuable technical alternative for known medication delivery devices. The medication delivery device according to the present invention e.g. has the advantage that the piston rod is driven back into the device body when a new cartridge is attached, without the user having to touch any part of the dosing mechanism and without any movement of the cartridge bung. The medication delivery device according to instant invention further provides the advantage of an easy replacement of the medication cartridge almost without application of pressure on the bung of the cartridge during resetting of the device and therefore without pressurization of the medication within the cartridge before the first setting and dispensing of a dose.

According to the invention, a medication delivery device is provided, comprising:
 a housing having a proximal and a distal end,
 a medication receptacle designed to be engaged with the housing
 a piston rod which is movable in a distal direction for medication delivery and
 a drive device for rotating the piston rod in a first rotational direction and thereby moving the piston rod in the distal direction for medication delivery.

The piston rod comprises two threaded sections, wherein a first threaded section is provided for threaded engagement with a reset element and a second threaded section is provided for threaded engagement with the drive device and the threads in the first and second threaded sections are oppositely disposed.

In an operational state the reset element is prevented from rotation with respect to the housing, the piston rod being prevented from moving in a proximal direction. In a resetting state the reset element is allowed to rotate with respect to the housing, the medication delivery device being resettable by rotating the piston rod and the reset element in a second rotational direction and moving the piston rod in the proximal direction.

The medication delivery device according to the present invention is designed such that, in the operational state the piston rod can be moved axially in the distal direction and rotated in one direction (the first rotational direction) with respect to the housing by the drive device for medication delivery and the piston rod is prevented from axial movement in the proximal direction with respect to the housing.

According to the present invention the medication delivery device is designed such that in the operational state, the reset element is prevented from rotation with respect to the housing. Preferably, the reset element is prevented from any movement (translational as well as rotational movement) with respect to the housing in the operational state. Preferably, the reset element is mounted within the housing such that it is prevented from axial movement with respect to the housing at any time and it is additionally prevented from rotation only in the operational state. Alternatively, the reset element can be mounted within the housing such that it is retained for rotational movement and for limited axial movement with respect to the housing in the resetting state and it is prevented from axial movement and from rotation with respect to the housing in the operational state.

Furthermore, the medication delivery device is designed such that in the resetting state, the piston rod is free to move axially in the proximal direction with respect to the housing (while rotating in the other direction—the second rotational direction). Preferably, the medication delivery device is designed such that in the resetting state, the piston rod is free to be wound back in the proximal direction with respect to the housing e.g. for resetting the piston rod when a new medication receptacle (e.g. a new cartridge or a cartridge holder with a new cartridge) is mounted on the distal end of the housing of the device.

According to a preferred embodiment of the present invention the medication delivery device is designed such that
 when the medication receptacle is engaged with the distal end of the housing the reset element is in the operational state and
 when the medication receptacle is disengaged from the distal end of the housing the reset element is in the resetting state.

According to this embodiment, the movement for engaging the medication receptacle with the housing results in the reset element being moved into a position or brought into a state in which it is rotatably locked with respect to the housing. This can be achieved e.g. by moving the reset element into a position in which it engages with features (e.g. with teeth or splines) of the housing or of another non-rotatable component of the medication delivery device or e.g. by moving another non-rotatable component into a position in which it engages with the reset element and prevents rotation thereof.

The present invention therefore further refers to a medication delivery device comprising:
 a housing having a proximal and a distal end,
 a medication receptacle designed to be engaged with the distal end of the housing
 a piston rod which is movable in a distal direction for medication delivery and
 a drive device for rotating the piston rod in a first rotational direction and thereby moving the piston rod in the distal direction for medication delivery.

The piston rod is threadedly engaged with a reset element. Preferably, the piston rod comprises two threaded sections, wherein a first threaded section is provided for threaded engagement with the reset element and a second threaded section is provided for threaded engagement with the drive device and the threads in the first and second threaded sections are oppositely disposed.

When the medication receptacle is engaged with the housing the reset element is prevented from rotation with respect to the housing, the piston rod thereby being prevented from moving in a proximal direction. When the medication receptacle is disengaged from the housing the reset element is allowed to rotate with respect to the housing, the medication delivery device being resettable by rotating the piston rod and the reset element in a second rotational direction and moving the piston rod in the proximal direction. The device is therefore in an operational state when the medication receptacle is engaged with the housing and in a resetting state when the medication receptacle is disengaged from the housing.

According to a preferred embodiment of the present invention the medication receptacle is designed to be engaged with the distal end of the housing by engagement of first engagement means and second engagement means. The first engagement means and the second engagement means are movable into engagement e.g. by a movement of the medication receptacle which comprises a rotational movement without axial movement of the medication receptacle (e.g. a movement which ends in a rotational movement without axial movement of the medication receptacle) with respect to the housing (or vice versa, by a movement of the housing which comprises a rotational movement without axial movement of the housing (e.g. a movement which ends in a rotational movement without axial movement of the housing) with respect to the medication receptacle). The reset element can thus preferably be brought into the operational state during a rotational movement of the medication receptacle while the medication receptacle does not move axially with respect to the housing or during a rotational movement of the housing while the housing does not move axially with respect to the medication receptacle.

However, the medication receptacle can be engaged with the housing by any engagement means known by those skilled in the art.

The medication receptacle of the medication delivery device can comprise an actuation means for bringing (and preferably also for holding) the reset element in an operational state in which the reset element preferably guides the piston rod for medication delivery. The housing and the medication receptacle can be movable into engagement e.g. by a movement which comprises, preferably ends in a rotational movement without axial movement of the actuation means with respect to the housing, the actuation means thereby bringing the reset element in the operational state.

The medication delivery device can be designed such that, by a movement, e.g. a rotational movement, of the actuation means, the actuation means is directly or indirectly interacting with the reset element for bringing the same in the operational state and thereby bringing the medication delivery device in an operational state for medication delivery in which the reset element is prevented from rotating with respect to the housing and in which the piston rod is prevented from moving in the proximal direction.

In a preferred embodiment of the present invention first and second engagement means of the housing and the medication receptacle are designed such that when the medication receptacle and the housing are moved into engagement the actuation means are first rotated and moved axially with respect to the housing and are thereafter rotated without being moved axially, thereby bringing the reset element in the operational state. When the first and second engagement means are moved out of engagement (and thus when the medication receptacle is disengaged from the housing), the reset element preferably moves out of or is brought out of the operational state into another position (resetting state) in which it no longer guides or holds the piston rod.

According to a preferred embodiment of the present invention the medication receptacle or an insert of the medication receptacle comprises the first engagement means and the housing or an insert of the housing comprises the second engagement means.

The first engagement means can e.g. be a thread of the medication receptacle (preferably an external thread) and the second engagement means an engaging element of the housing or of an insert of the housing for engagement with the thread of the medication receptacle, wherein the distal end of the thread of the medication receptacle merges into an annular groove such that the medication receptacle is engaged with the housing by first rotating and moving proximally with respect to the housing and then only rotating with respect to the housing. The pure rotation at the end of the engaging movement is caused by the engaging element moving along the annular groove which does not have a pitch (i.e. the lead of which is zero). Preferably the annular groove is only a part annular groove which runs around a part (e.g. ⅙) of the perimeter of an essentially tubular end of the medication receptacle. Alternatively, the thread/annular groove can be part of the housing and the medication receptacle can comprise the engaging element.

Alternatively, the distal end of the housing can e.g. be provided with an insert comprising the second engagement means and designed to engage with the first engagement means at the proximal end of the medication receptacle, the insert being secured against rotation but being free to move axially with respect to the housing (limited axial movement), wherein distal axial movement of the insert is limited by a retaining means. Particularly, the insert of the housing can comprise an inner thread as a second engagement means for engaging a first engagement means which is an outer thread at the proximal end of the medication receptacle, the medication receptacle comprising the actuation means and being rotated and moved axially with respect to the insert and the housing in a first step for engaging the medication receptacle with the housing and the medication receptacle being rotated while axial movement of the medication receptacle is prevented with respect to the housing in a second step for engaging the medication receptacle with the housing, the insert being moved in the distal direction by the rotation of the medication receptacle during the second step. The insert can be moved in the distal direction e.g. until the insert abuts the retaining means or until the inner thread of the insert ends.

According to a preferred embodiment of the present invention the insert is a movable sleeve with an internal thread and the retaining member is a retaining ring which limits the distal axial movement of the sleeve. The retaining ring is attached to the distal end of the housing such that it is prevented from rotation and from axial movement with respect to the housing. Furthermore, a spring member is provided to move the sleeve against a proximal axial stop means (e.g. an annular rib) within the housing when the medication receptacle is not engaged with the housing of the device. The spring member preferably abuts the proximal side of the retaining ring on one side and the distal side of the movable sleeve on the other side. The sleeve is engaged with the housing such that it is allowed to move linearly and restrained from rotation. When the housing and the medication receptacle are moved into engagement, an external thread on the proximal end of the medication receptacle engages the internal thread of the sleeve. Therefore the medication receptacle is screwed into the distal end of the housing, until the proximal edge or shoulder of the medication receptacle abuts the distal side of the retaining ring. This abutment prevents a further linear proximal movement of the medication receptacle. However, a further rotation of the medication receptacle is allowed, thereby causing the sleeve to move linearly in the distal direction against the force of the spring means until the sleeve abuts the proximal side of the retaining ring. This abutment ends the engaging movement of the housing and the medication receptacle. The pure rotation of the medication receptacle at the end of the engaging movement is used to bring a reset element into its operational state in which it guides the piston rod for medication delivery.

In all of the embodiments of the present invention, the reset element is preferably a nut means which is threadedly engaged with the piston rod, preferably with an external thread of the piston rod. According to a preferred embodiment of the present invention the reset element is a nut means which is threadedly engaged with the piston rod and which is engaged with a locking means in the operational state and which is disengaged from the locking means in the resetting state.

According to a preferred embodiment of the present invention the drive device comprises a drive sleeve and a second threaded section of the piston rod is provided for threaded engagement with the drive sleeve.

In this embodiment, the medication delivery device can be designed such that the drive sleeve is threadedly engaged with (the second threaded section of) the piston rod and when the drive sleeve drives the piston rod in distal direction for medication delivery, the drive sleeve is moved axially and is prevented from rotation with respect to the housing, thereby causing axial distal movement and rotation of the piston rod. The displacement of the drive sleeve in the distal direction (without rotating) with respect to the housing during medication delivery results in a displacement of the drive sleeve in the distal direction with respect to the piston rod. This displacement causes the piston rod to rotate in the first rotational direction due to the threaded engagement of the drive sleeve with the second threaded section of the piston rod. This rotational movement of the piston rod winds the piston rod in the distal direction due to the threaded engagement of the reset element with the first threaded section of the piston rod. The piston rod therefore pushes a piston within the medication receptacle in the distal direction, thereby delivering medication out of the medication receptacle.

A mechanical advantage can be achieved e.g. if the thread of the second threaded section (which is engaged with the drive device, preferably with the drive sleeve) has a larger pitch than the thread of the first threaded section (which is engaged with the reset element). Therefore, according to a preferred embodiment of the present invention the piston rod has a thread in the first threaded section with a first pitch and a thread in the second threaded section with a second pitch, wherein the first pitch is smaller than the second pitch (the lead of the thread in the first threaded section being smaller that the lead of the thread in the second threaded section).

Preferably, the medication delivery device according to the present invention further comprises stop means, the stop means being designed such that
  during dose setting the drive sleeve is not allowed to move axially without rotation with respect to the housing and
  during dose delivery rotation of the drive sleeve with respect to the housing is not allowed while the drive sleeve is allowed to move axially in the distal direction with respect to the housing.

The stop means can e.g. comprise a clutch means which is non-rotatably engaged with the drive sleeve. Preferably, the clutch means is located between a dose dial sleeve and the drive sleeve and is provided to couple and decouple the dose dial sleeve and the drive sleeve.

The medication delivery device according to the present invention preferably comprises a dosing mechanism which includes the piston rod and the drive device. Further, the dosing mechanism can comprise:
  a dose dial sleeve having a helical thread engaged with a helical thread of the housing, the drive sleeve being releasably coupled with the dose dial sleeve and
  a clutch means located between the dose dial sleeve and the drive sleeve,
wherein,
a) when the dose dial sleeve and the drive sleeve are coupled (by means of the clutch means), both are allowed to rotate with respect to the housing, and
b) when the dose dial sleeve and the drive sleeve are de-coupled, rotation of the dose dial sleeve with respect to the housing is allowed, whilst rotation of the drive sleeve with respect to the housing is not allowed and axial movement of the drive sleeve is allowed in the distal direction thereby transferring a force in the distal direction to the piston rod.

Preferably, when the dose dial sleeve and the drive sleeve are coupled (by means of the clutch means), both are allowed to rotate and move axially with respect to the housing whilst both are not allowed to move axially without rotating with respect to the housing (e.g. by the dose dial sleeve being engaged with the housing via a helical thread). According to a preferred embodiment of the present invention, the dose dial sleeve and the drive sleeve are coupled during dose setting and decoupled during dose delivery.

The dose dial sleeve and the drive sleeve are preferably coupled during resetting of the medication delivery device (in the resetting state). Preferably, in the resetting state the drive sleeve is not allowed to move axially. Alternatively and most preferably, in the resetting state the drive sleeve is only allowed to move axially in combination with a rotational movement (e.g. the drive sleeve being indirectly coupled to a thread of the housing via a clutch means and a dose dial sleeve) and not allowed to move axially without rotating. Consequently in the resetting state, when a force is applied (e.g. by a user) to push the distal end of the piston rod (e.g. a pressure foot) in the proximal direction, the piston rod rotates together with the reset element in the second rotational direction. The piston rod is thereby wound in the proximal direction by means of the threaded engagement between the drive sleeve and the second threaded section while the drive sleeve does not move axially.

According to a preferred embodiment of the present invention the pitch (and lead) of the helical thread of the dose dial sleeve which is engaged with the helical thread of the housing is the same as the pitch (and lead) of the thread in the second threaded section of the piston rod. In this case the displacement of the dose dial sleeve with respect to the housing is identical to the displacement of the drive sleeve with respect to the piston rod during dose setting.

In all above mentioned embodiments, the medication delivery device can comprise a locking means which is non-rotatable with respect to the housing and which is engageable with the reset element, thereby locking the reset element for preventing rotation of the reset element with respect to the housing in the operational state.

Preferably, the locking means is splined to the housing or to an insert of the housing, thereby being allowed to move axially but being prevented from rotating with respect to the housing. Preferably, the locking means is allowed to move axially only for a limited axial movement with respect to the housing. Alternatively, the locking means can be fixed to the housing or even be part of the housing and therefore be prevented from any movement with respect to the housing.

When the reset element is engaged with a locking means in the operational state, the piston rod is preferably prevented from rotation in one rotational direction and from axial movement in the proximal direction with respect to the housing but is allowed to rotate in the other rotational direction and to move axially in the distal direction with respect to the housing for medication delivery.

The reset element or the locking means of the medication delivery device according to the present invention can comprise a shape which interacts with the shape of an actuation means for driving the locking means and the reset element into engagement by a rotational movement (preferably without an axial movement) of the actuation means with respect to the housing.

Particularly, at least one inclined surface can be arranged on the actuation means and at least one correspondingly inclined surface can be arranged on the reset element or on the locking means, wherein the inclined surfaces are formed such that for interaction of the actuation means and the reset element or of the actuation means and the locking means the inclined surfaces can glide along each other.

Preferably, the actuation means comprises at least one protrusion with the inclined surface fixedly or movably arranged on the actuation means or it comprises at least one ramp with an inclined surface for interacting with the reset element or the locking means e.g. by a rotational movement of the actuation means in one direction with respect to the housing, thereby driving the reset element and the locking means into engagement.

The locking means and the reset element can e.g. comprise face teeth which interlock when the locking means and the reset element are engaged in the operational state. In the resetting state, the face teeth are disengaged and the locking means and the reset means are therefore disengaged.

Further, the medication delivery device is preferably designed such that the locking means disengages from the reset element under the force of a biasing means e.g. when the medication receptacle is disengaged from the housing. The biasing means is preferably a spring which forces the reset element and the locking means apart when the medication receptacle is separated from the housing of the medication delivery device. Most preferably the biasing means moves the locking means axially away from the reset element when the medication receptacle is disengaged from the distal end of the housing, thereby disengaging the locking means and the reset element.

Additionally or alternatively, the medication delivery device can be designed such that when the medication receptacle is disengaged from the housing, the locking means is disengaged from the reset element, whereby the reset element is free to rotate with respect to the housing.

When the locking means and the reset element are disengaged in this embodiment, the reset element is no longer in the operational state, but in the resetting state. According to a preferred embodiment of the present invention the piston rod is free to move proximally when the locking means is disengaged from the reset element.

Preferably, the medication receptacle is a cartridge holder which is designed to receive a cartridge filled with medication. The cartridge holder is designed to be engaged with a distal end of the housing. Alternatively the medication receptacle can e.g. be a cartridge having first engagement means for engaging second engagement means of the housing. A cartridge filled with medication is preferably a tubular sleeve containing the medication and being closed by a piston at one end and by a piercable septum at the other end. When the piston is moved proximally in the cartridge, the medication is dispensed e.g. through a needle which protrudes through the septum and which is in communication with the medication (e.g. insulin).

According to a preferred embodiment of the present invention the medication receptacle (or an insert or attachment of the medication receptacle) and the housing (or an insert or attachment of the housing) can additionally be provided with snap-in features by means of which the medication receptacle and the housing are held in engagement during normal use of the medication delivery device, especially during dose setting and medication delivery. Furthermore the snap-in features can provide an audible and/or tactile feedback to the user, when the medication receptacle is safely attached to the housing.

The medication delivery device can be a pen-type device and/or an injector-type device. The medication delivery device can comprise a needle or be a needle-free device.

The term "medication delivery device" according to instant invention shall mean a single-dose or multi-dose, disposable or re-usable device designed to dispense a dose of a medicinal product, preferably multiple selected doses, e.g. of insulin, growth hormones, low molecular weight heparins, and their analogues and/or derivatives etc. Said device may be of any shape, e.g. compact or pen-type. Dose delivery may be provided through a mechanical (optionally manual) dosing mechanism or electrical dosing mechanism or electro-mechanical dosing mechanism or stored energy dosing mechanism, such as a spring, etc. Dose selection may be provided through a manual mechanism or electronic mechanism or electro-mechanical mechanism. Additionally, said device may contain components designed to monitor physiological properties such as blood glucose levels, etc. Furthermore, the said device may comprise a needle or may be needle-free. Preferably, the term "medication delivery device" shall mean a re-usable multi-dose pen-type device having mechanical and manual dose selection and dose delivery mechanisms, which is designed for regular use by persons without formal medical training such as patients. Preferably, the medication delivery device is of the injector-type. Most preferably the medication delivery device is designed to deliver a fluid medication.

The term "medication receptacle" in the context of the present invention shall preferably mean a cartridge containing a medication or a cartridge assembly, most preferably a cartridge holder for receiving a cartridge containing a medication. Furthermore, the terms "medication receptacle" and "cartridge" and "cartridge assembly" are exchangeable in the context of the present invention. This means that by using the term "medication receptacle", any meaning of the terms "cartridge" or "cartridge assembly" is included, and vice versa.

The term "cartridge holder" according to instant invention shall mean any component and/or components designed to house a medicament cartridge containing a medication to be delivered by the medication delivery device. Said cartridge holder may be of any shape, e.g. cylindrical and/or tubular. In general, the cartridge holder may be unitary or a multipart component of a cylindrical tubular or non-tubular shape. It may be made of any suitable material known by a person skilled in the art, e.g. of a transparent material. Further the cartridge holder or an insert of the cartridge holder is preferably provided with engagement means, e.g. helical threads or part threads or bayonet or the like, on an external and/or internal surface of the distal end and/or proximal end of the cartridge holder or the insert designed for engagement with corresponding engagement means located on an exterior and/or interior surface of a housing, an insert of the housing and/or a needle assembly. In a preferred embodiment the cartridge holder is of a unitary tubular design having an external thread located at its proximal end.

The term "housing" according to instant invention shall preferably mean any exterior housing ("housing", "body", "shell") or interior housing ("insert", "inner body") having an engaging means, such as a helical thread, spline or any other suitable means known by a person skilled in the art. The housing may be designed to enable the safe, correct, and comfortable handling of the medication delivery device or any of its mechanisms. Usually, it is designed to engage with any of the inner components of the medication delivery device (e.g., a dosing mechanism, cartridge, plunger, piston rod), to house, fix, guide, and/or protect by limiting the exposure to contaminants, such as liquid, dust, dirt etc. In general, the housing may be unitary or a multipart component of tubular or non-tubular shape. The exterior housing may also serve to house a cartridge from which a number of doses of a medicinal product may be dispensed.

The term "reset element" according to the present invention shall preferably mean any component designed to prevent the resetting of the medication delivery device when the reset element and therefore the medication delivery device are in the operational state and designed to enable the resetting of the medication delivery device when the reset element and therefore the medication delivery device are in the resetting state. The reset element can therefore assume a resetting state and an operational state. The reset element preferably also has the function of guiding the piston rod in the operational state during medication delivery. For this guiding function of the reset element preferably comprises a shape for interacting with a corresponding shape of the piston rod, e.g. an inner thread for engaging an outer thread of the piston rod or a non circular opening for holding a piston rod with a corresponding non-circular form or a piston rod with a section having the corresponding non-circular form.

The term "operational state" according to the present invention shall preferably mean a position or state of the reset element in which the reset element prevents the resetting of the medication delivery device, i.e. it directly or indirectly prevents a movement of the piston rod in the proximal direction. Preferably, the operational state is furthermore a position or state of the reset element in which the reset element guides and/or holds the piston rod. The reset element and therefore the medication delivery device are preferably in the operational state when the medication delivery device is used for dose setting and medication delivery.

The term "resetting state" according to the present invention shall preferably mean a position or state of the reset element in which the reset element allows the resetting of the medication delivery device, i.e. it directly or indirectly allows a movement of the piston rod in the proximal direction. The reset element is preferably in the resetting state when the medication delivery device is disassembled (i.e. the medication receptacle disengaged from the housing) for replacing an empty cartridge by a new cartridge filled with medication.

The term "nut means" according to instant invention shall preferably mean any component designed to be threadedly engaged with a piston rod, preferably to act as a guide for the piston rod. Further, the term "nut means" according to instant invention shall mean any component with a threaded circular opening that may be a single or multiple part component. According to a preferred embodiment of the present invention, the reset element is a nut means. In a further more specific embodiment the nut means is free to rotate with respect to the housing when not engaged with a locking means of the medication delivery device. According to one embodiment of the present invention, the nut means is free to rotate with respect to the housing and is secured against linear axial movement with respect to the housing when not engaged with a locking means of the medication delivery device, but is secured against rotation and linear axial movement with respect to the housing when engaged with the locking means. Most preferably, the nut means is free to rotate and retained for limited linear axial movement with respect to the housing when not engaged with a locking means of the medication delivery device, but is secured against rotation and linear axial movement with respect to the housing when engaged with the locking means. In an even more specific embodiment the nut means has a textured surface, for example a set of face teeth (saw teeth, dog teeth, crown teeth, or the like) or any other suitable frictional face, preferably to engage a textured surface of another component of the device, most preferably of a locking means.

The term "locking means" according to instant invention shall preferably mean any component that is part of the housing, fixed to the housing or engaged with the housing or with an insert of the housing such that it is prevented from rotational movement with respect to the housing, most preferably such that it is allowed to move longitudinally but is prevented from rotational movement with respect to the housing. In a preferred embodiment the locking means has a textured surface, for example a set of face teeth (saw teeth, dog teeth, crown teeth, or the like) or any other suitable frictional face. In a more preferred embodiment a non-rotatable locking means is designed to engage with the reset element, thereby preventing rotation of the reset element with respect to the housing. In a more specific preferred embodiment of instant invention, a textured surface of the non-rotatable locking means engages with a textured surface of a reset element (preferably a nut means) in the operational state to prevent the reset element from rotating as long as a medication receptacle (preferably a cartridge holder) is engaged with the housing.

The term "actuation means" according to instant invention shall preferably mean any component of the medication delivery device and/or part of a component of the medication delivery device designed to move any other component(s) of the medication delivery device into and/or out of engagement with another component of the medication delivery device and/or components of the medication delivery device and/or to maintain any component(s) of the medication delivery device in engagement. Preferably the actuation means is a means to actuate a locking means in order to move the locking means into engagement with the reset element. Alternatively the actuation means can be a means to actuate the reset element in order to move the reset means into engagement with a locking means. In a preferred embodiment of instant invention, the actuation means shall form an integral part of the proximal end of the medication receptacle, e.g. the cartridge holder of the medication delivery device.

The term "stop means" according to instant invention shall mean any feature(s) and/or component(s) of the medication delivery device designed to prevent axial and/or rotational movement of any component and/or components at least in one direction. In a preferred embodiment of instant invention, the term "stop means" shall mean any feature perpendicular to the distal-proximal axis of the medication delivery device (particularly any planar surface feature perpendicular to the distal-proximal axis of the medication delivery device) designed to prevent axial movement of a component in one direction when this component abuts the perpendicular feature. According to another preferred embodiment of the present invention the term "stop means" shall mean any feature which provides a radial or rotational stop designed to prevent rotational movement of a component in one rotational direction when an abutment element of the component abuts the radial or rotational stop feature.

In still a further preferred embodiment of instant invention, the term "stop means" shall mean a component ("end stop") of the dosing mechanism which prevents the setting of a dose which exceeds the amount of medication left in the medication receptacle. Preferably the end stop is a component which is secured against rotation but allowed to move axially with respect to a housing and which shall prevent at least one component of the dosing mechanism from rotational and/or axial movement when a final dose has been set, thereby preventing the setting of a dose which exceeds the amount of medication left in the cartridge. Furthermore, the "end stop" shall preferably have a helical thread on an exterior surface designed to engage with an interior helical thread of a dose dial sleeve of the dosing mechanism or of an insert of a dose dial sleeve of the dosing mechanism. Preferably the lead of an external helical thread of the said dose dial sleeve for threaded engagement with the housing shall be greater than the lead of the internal helical thread of the dose dial sleeve for threaded engagement of the said end stop.

The term "engaging" according to instant invention shall mean the interlocking of two or more components of the dosing mechanism/medication delivery device, by means of e.g. a spline, thread, or meshed teeth connection, preferably the interlocking of threads of components ("threadedly engaged").

The term "engagement means" according to the present invention shall preferably mean any means known to those skilled in the art which can be used to engage two or more components of a medication delivery device, e.g. full or part threads, grooves, engaging elements which mesh with threads and/or grooves or means which form a bayonet lock.

The term "disengaging" according to instant invention shall mean the unlocking of two or more components of the dosing mechanism/medication delivery device. According to one example the term "disengaging" according to instant invention shall mean the unlocking of two or more components of the dosing mechanism/medication delivery device under the force of a biasing means. Two components can also be disengaged by the force of a user of the device, e.g. by a patient unscrewing the medication receptacle from the housing.

The term "biasing means" according to instant invention shall preferably mean any component that is provided for exerting a force on a component and/or components to ensure that the component and/or components are forced together (e.g. into engagement) or forced apart (e.g. out of engagement). Preferably the biasing means may be manufactured from any suitable flexible energy storage material known by a person skilled in the art (e.g. metal, rubber or plastics) and may take any suitable form, e.g., a spring. In a more preferred embodiment the biasing means is a spring component e.g. located between the reset element and the locking means. In another preferred embodiment the biasing means is a spring component located between a nut means and a locking means and located in the housing.

The term "distal end" according to instant invention shall mean the end of the device or a component of the device which is closest to the dispensing end of the device. Preferably a needle assembly is provided at the distal end of the medication delivery device of the present invention the needle of which can be inserted into the skin of a patient for medication delivery.

The term "proximal end" according to instant invention shall mean the end of the device or a component of the device which is furthest away from the dispensing end of the device. Preferably a button is provided at the proximal end of the medication delivery device of the present invention which is pushed for dose delivery.

The term "dosing mechanism" according to instant invention shall mean any component and/or components and/or assembly designed to allow a user to select and/or set a dose to be dispensed and/or to provide and/or to transmit a force necessary to dispense a dose of a medication. Said dosing mechanism may be composed of mechanical and/or electro-mechanical and/or electronic components. Additionally, the dosing mechanism may be housed by and/or engaged with the device housing or may be an independent assembly. The dosing mechanism of instant invention comprises a piston rod and a drive device for moving the piston rod in the distal direction for medication delivery. Preferably, the dosing mechanism of instant invention comprises a drive sleeve and a dose dial sleeve. More preferably, the dosing mechanism of instant invention comprises a drive sleeve, a dose dial sleeve, a clutch means, a dose dial grip and a button means.

The term "piston rod" according to instant invention shall mean a component adapted to operate through/within the housing, designed to translate axial movement (preferably towards the distal end) through/within the medication delivery device, preferably from a drive sleeve to the piston of the cartridge, for the purpose of discharging/dispensing a medication from the cartridge, preferably an injectable product. Said piston rod may be flexible or not. It may be a simple rod, a lead-screw, a part of a rack and pinion system, a part of a worm gear system, or the like. The "piston rod" shall further mean a component having a circular or non-circular cross-section. It may be made of any suitable material known by a person skilled in the art.

In a preferred embodiment, the piston rod comprises at least two, more preferably two, external and/or internal helical threads (threaded sections). In another preferred embodiment of the piston rod according to instant invention, a first helical thread (first threaded section) is located at a distal end and a second helical thread (second threaded section) is located at a proximal end of the said piston rod, whereby the said threads of the threaded sections have opposite dispositions. In another preferred embodiment the piston rod of instant invention comprises at least two threaded sections with threads having the same leads and the same pitches at the distal and the proximal end. In yet another preferred embodiment of instant invention the lead and the pitch of the second helical thread of the piston rod shall be greater than the lead and the pitch of the first helical thread. More preferred, the ratio of the leads of the helical threads of the said first and the second helical threads is in the range of 1:1.01 to 1:20, even more preferred in the range of 1:1.1 to 1:10, most preferred 1:2.3. Preferably, one of the said threads (the thread of the second threaded section) is designed to engage with the drive sleeve. Preferably another of the said threads (the thread of the first threaded section) is designed to engage with the reset element, more preferably with a nut means. According to a most preferred embodiment of the present invention, a first external threaded section of the piston rod with a thread having a smaller lead is designed to engage with an internal thread of a nut means and a second external threaded section of the piston rod with a thread having a larger lead is designed to engage with an internal thread of a drive sleeve. In a further preferred embodiment of instant invention, the piston rod is provided with a stop means designed to limit the proximal axial movement of an end stop. The stop means may e.g. be the start of one of the external threads of the piston rod.

The term "dose dial sleeve" according to instant invention shall preferably mean a component of the medication delivery device which is directly or indirectly used to select/dial a dose of medication to be delivered. Additionally or alternatively the dose dial sleeve is designed to indicate a selected dose of a dispensable product (medication). This may be achieved by use of markings, symbols, numerals, etc., e.g. printed on the external surface of a sleeve or an odometer, or the like. Most preferably the dose dial sleeve is marked by means of laser printing. In a preferred embodiment of the present invention, the dose dial sleeve is an essentially tubular component of essentially circular cross-section having either:

both an internal and external thread, or
an internal thread, or
an external thread.

Preferably, the dose dial sleeve comprises an external thread for engaging an internal thread of the housing or of an insert of the housing. Preferably, the dose dial sleeve according to instant invention comprises an external helical thread having a lead, which is similar to, preferably the same as the lead of an internal helical thread of the drive sleeve. In a more specific embodiment of instant invention, the dose dial sleeve is provided with a plurality of radially extending members adapted to abut a corresponding plurality of radial stops provided within the housing or an insert of the housing. These radial stop means are preferably provided for stopping a further winding of the dose dial sleeve out of the housing when a dose is set and/or for stopping the further winding of the dose dial sleeve into the housing when a dose has been dispensed.

The term "drive device" according to the present invention shall preferably mean any component and/or components and/or assembly designed to transmit a force to the piston rod for dispensing a dose of a medication. Said drive device may be composed of mechanical and/or electro-mechanical and/or electronic components. The drive device may be housed by and/or engaged with the housing or may be an independent assembly. Preferably, the drive device of instant invention comprises a drive sleeve. More preferably, the drive device of instant invention comprises a drive sleeve, a clutch means and a button means.

The term "drive sleeve" according to instant invention shall preferably mean any component for directly or indirectly driving the piston rod in a distal direction for medication delivery, most preferably for driving the piston rod directly. According to a preferred embodiment of the present invention, the drive sleeve is an essentially tubular component of essentially circular cross-section. In a preferred embodiment the drive sleeve is engaged with the piston rod. Preferably the drive sleeve comprises an internal thread for engaging an external thread of the piston rod. The drive sleeve is further preferably releasably coupled to the dose dial sleeve, most preferably by a clutch means.

The term "thread" or "helical thread" according to instant invention shall preferably mean a full or part thread, e.g., a cylindrical spiral rib/groove, located on the internal and/or external surface of a component of the medication delivery device, having an essentially triangular or square or rounded section designed to allow continuous free rotational and axial movement between components. Optionally, a thread may be further designed to prevent rotational or axial movement of certain components in one direction by being non-overhaulable.

The term "lead" according to instant invention shall preferably mean the axial distance a nut would advance in one complete revolution; preferably "lead" shall mean the axial distance through which a component having a helical thread, i.e. dose dial sleeve, drive sleeve, piston rod, etc., of the dosing mechanism travels during one rotation. Therefore the lead is a function of the pitch of the thread of the relevant component.

The term "pitch" according to instant invention shall preferably mean the distance between consecutive contours on a helical thread, measured parallel to the axis of the helical thread.

One aspect of the present invention provides a medication delivery device according to instant invention for dispensing a medicinal product preferably for dispensing a pharmaceutical formulation (e.g. solution, suspension etc.) comprising an active compound selected from the group consisting of insulin, growth hormone, low molecular weight heparin, their analogues and their derivatives.

The invention further refers to a method of manufacturing or assembling a medication delivery device according to one of the above-mentioned embodiments. This method preferably comprises the step of moving a medication receptacle into engagement with the distal end of the housing of the device by engaging first engagement means with second engagement means. The engaging action of the medication receptacle being engaged with the housing results in the reset element being brought in the operational state in which the reset element is prevented from rotating with respect to the housing and in which the reset element therefore prevents the proximal movement of the piston rod and consequently the resetting of the medication delivery device.

According to the invention, the use of a medication delivery device according to one of the above-mentioned embodiments of a medication delivery device for dispensing a medicinal product is also provided. The use preferably comprises the dispensing of a pharmaceutical formulation (e.g. a liquid medication like a solution, a suspension etc.) comprising an active compound selected from the group consisting of insulin, growth hormone, low molecular weight heparin, their analogues, and their derivatives.

Figure 1B:
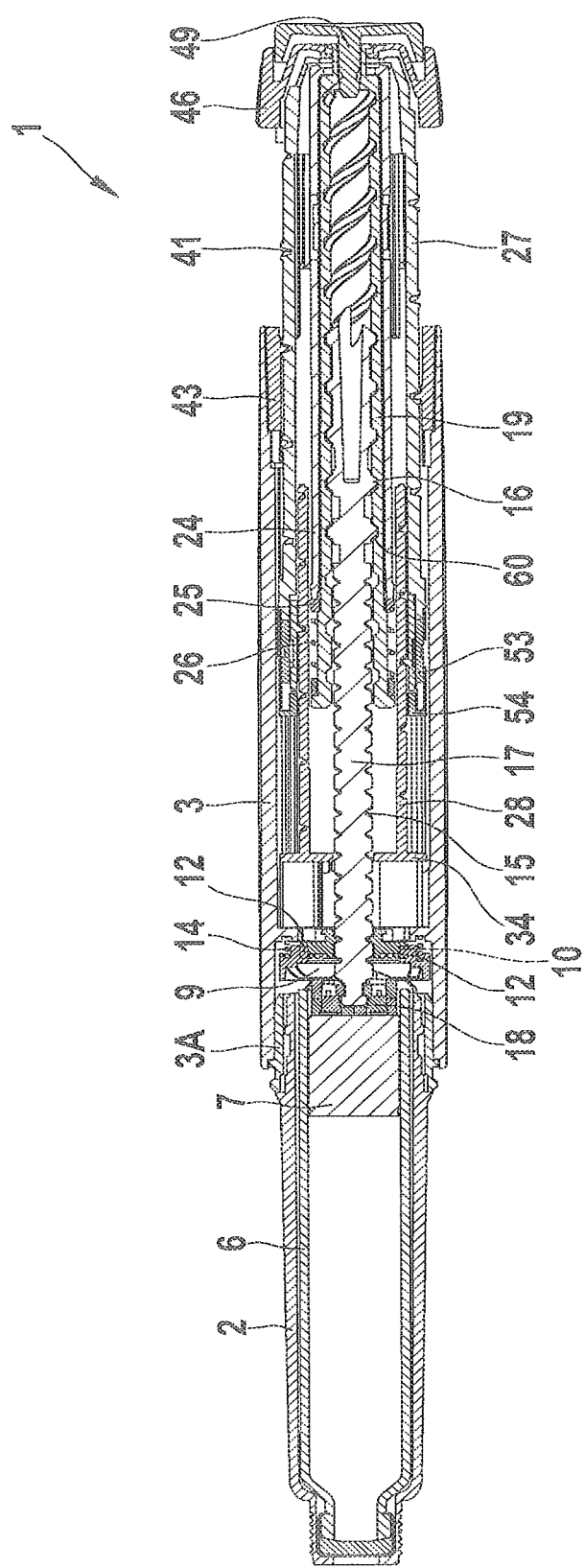
Figure 1C:
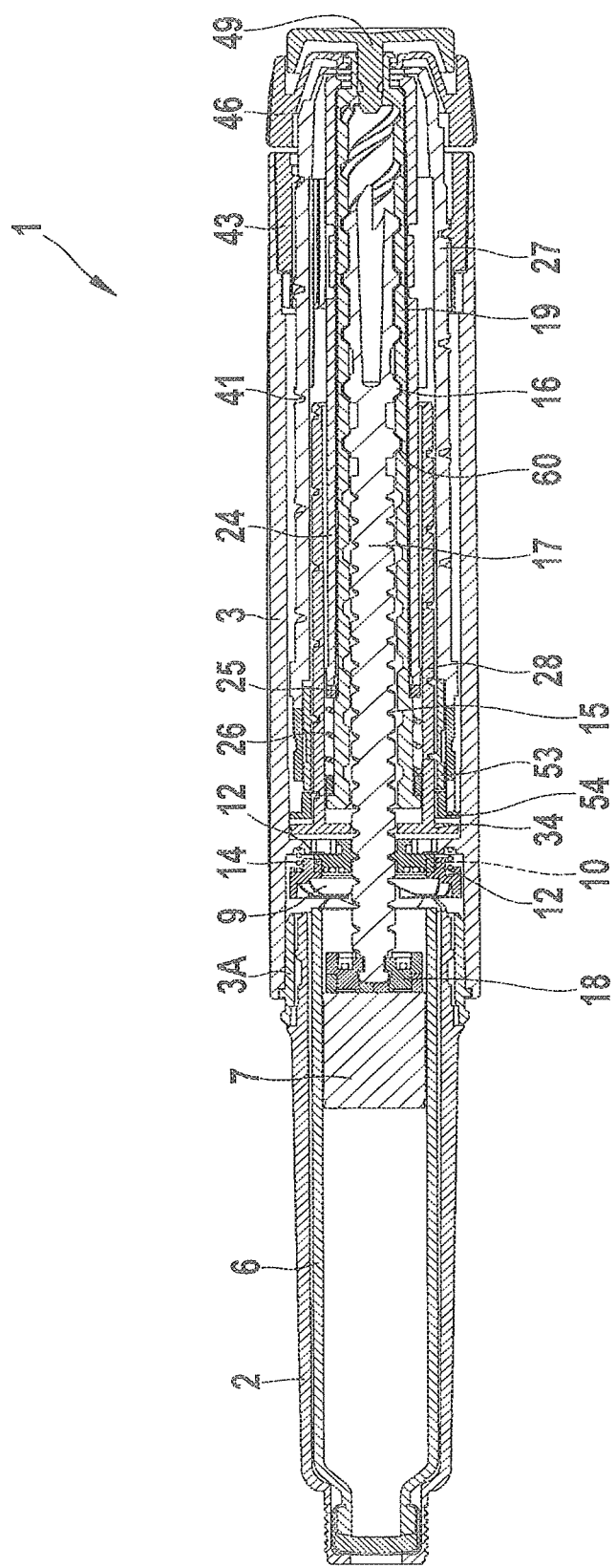
Figure 2A:
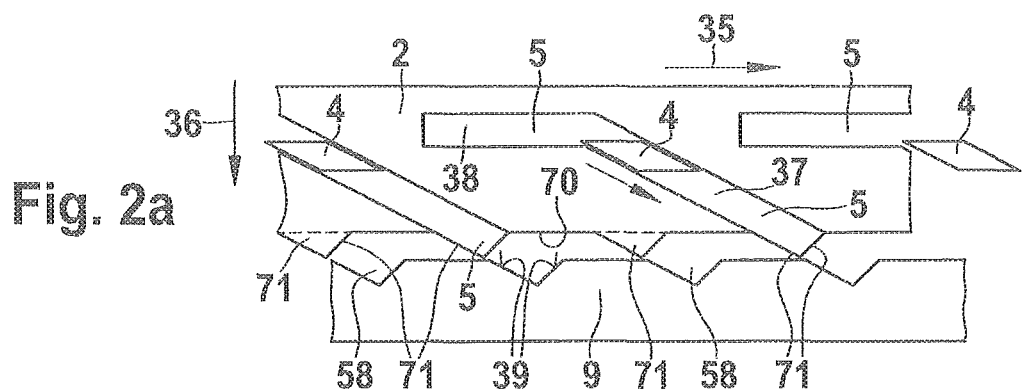
FIGS. 2a to 2c show schematically an embodiment of an actuation means interacting with locking means in three different states according to one embodiment of the present invention.
Figure 2B:
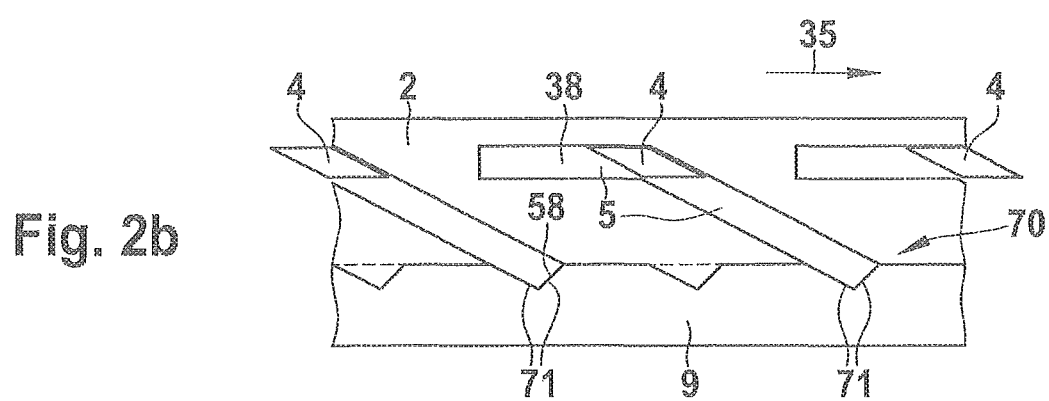
Figure 2C:
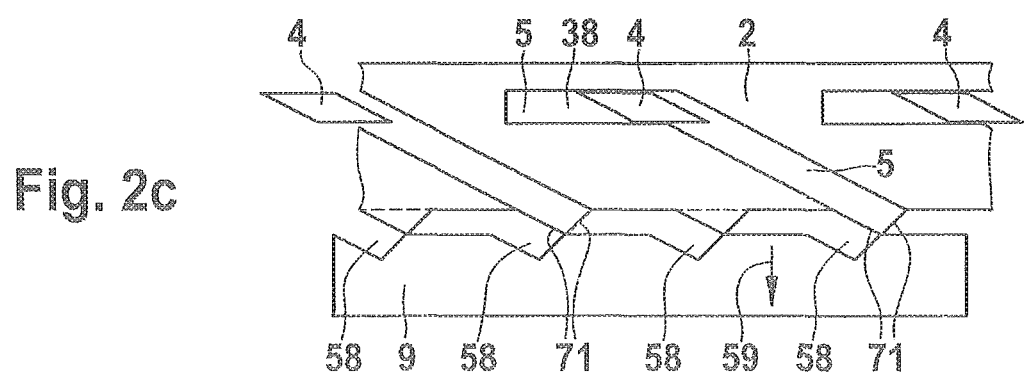
Figure 3:
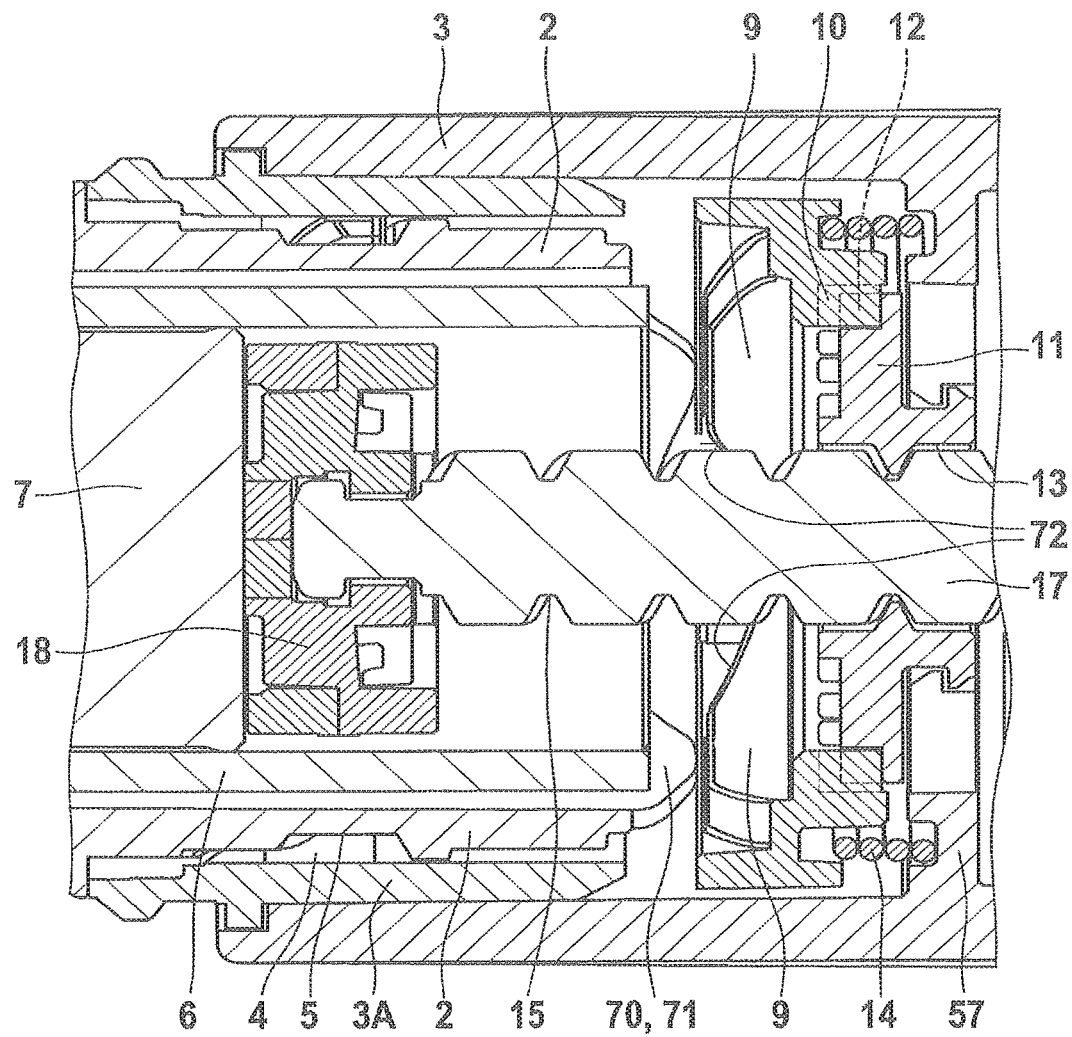
FIG. 3 shows a cross-sectional enlarged view of a middle part of the embodiment according to FIGS. 1a to 1c showing the reset element of the medication delivery device in the operational state.
Figure 4:
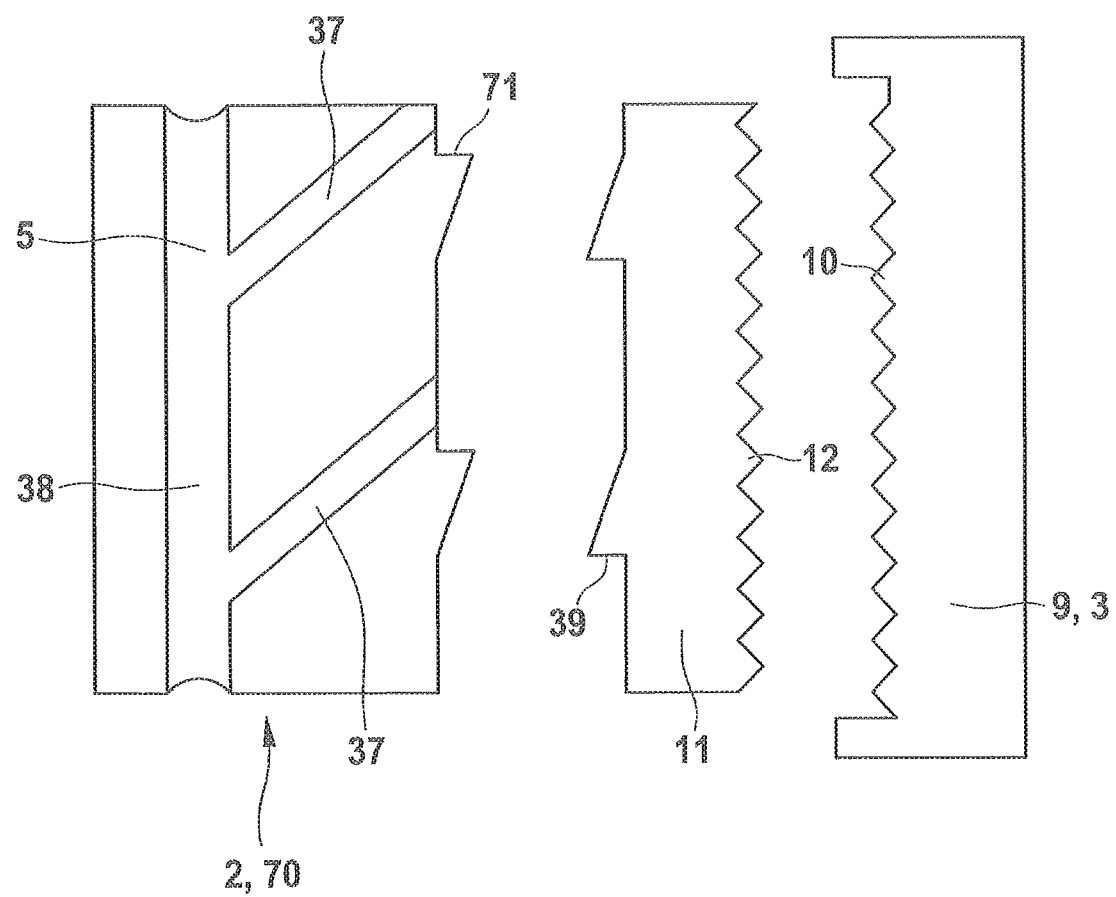
FIG. 4 shows schematically a different embodiment of the medication delivery device according to the present invention with a different arrangement of actuation means, locking means and reset element
Figure 5:
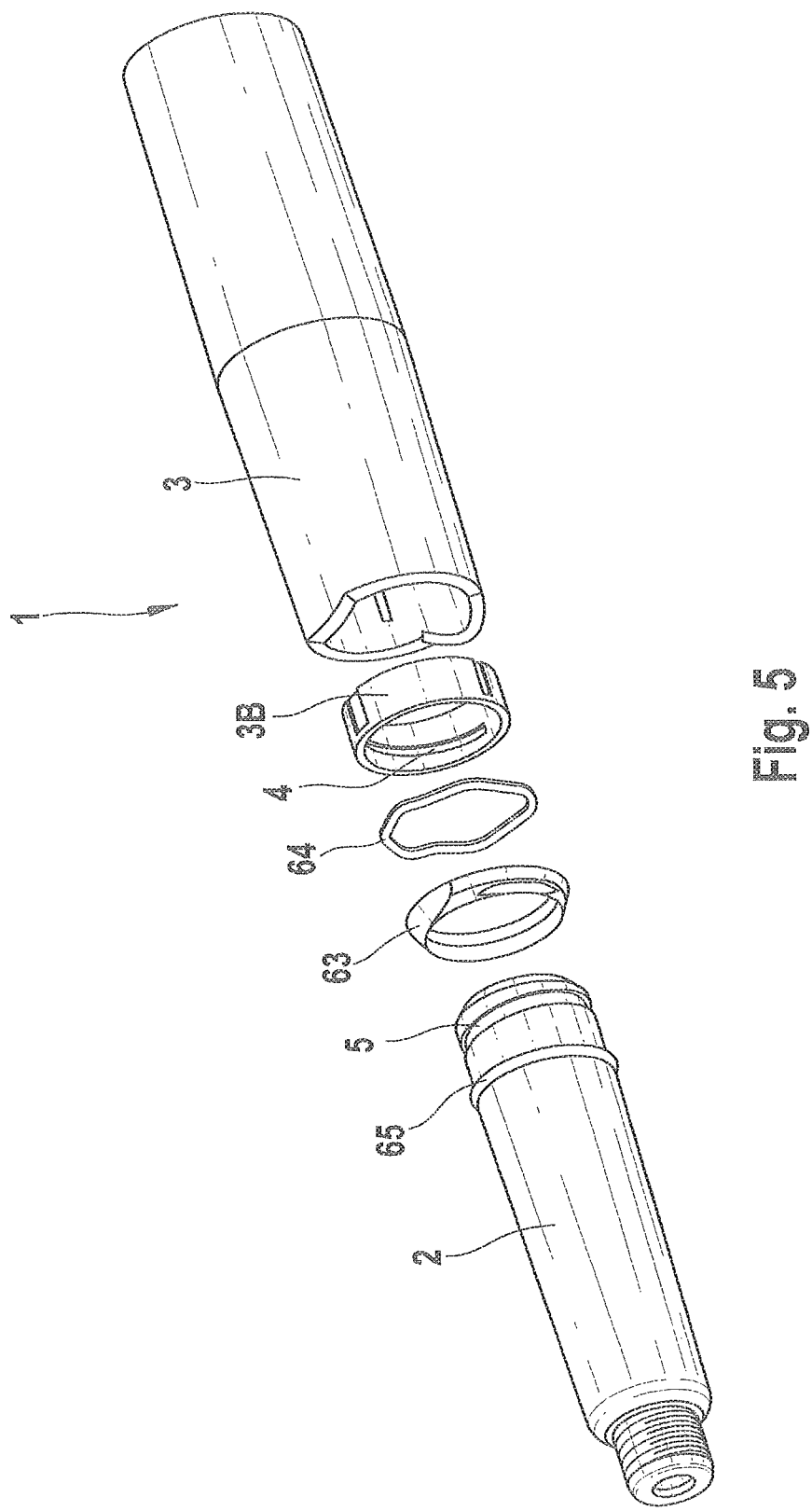
FIG. 5 shows another embodiment of a medication delivery device according to the invention.

Without any limitation, the present invention will be explained in greater detail below with reference to the drawings in which:

FIGS. 1a to 1c show a cross-sectional view of one embodiment of a medication delivery device according to the invention in three different states;

FIGS. 2a to 2c show schematically an embodiment of an actuation means interacting with locking means in three different states according to one embodiment of the present invention;

FIG. 3 shows a cross-sectional enlarged view of a middle part of the embodiment according to FIGS. 1a to 1c showing the reset element of the medication delivery device in the operational state, FIG. 4 shows schematically a different embodiment of the medication delivery device according to the present invention with a different arrangement of actuation means, locking means and reset element and FIG. 5 shows another embodiment of a medication delivery device according to the invention.

Referring first to FIGS. 1a to 1c, there is shown a medication delivery device in accordance with the present invention in three different positions.

The medication delivery device 1 comprises a cartridge holder 2 and a (exterior) housing 3. Preferably the housing 3 is lacquered. The distal end of the housing 3 is provided with an insert 3A which is immovably attached to the housing. The insert 3A is provided with second engagement means 4 for engaging first engagement means 5 of the cartridge holder 2. In the illustrated embodiment the insert 3A of the housing 3 is provided with a series of part threads formed on an interior surface of the insert 3A. The proximal end of the cartridge holder 2 is provided with first engagement means 5 for engaging the second engagement means 4 of the insert 3A. In the illustrated embodiment the cartridge holder 2 is provided with a thread, the distal end of which merges into a (part) annular groove (not shown) formed on an exterior surface of the cartridge holder 2. The cartridge holder 2 is secured within the distal end of the housing 3 by the engagement of the second engagement means 4 of the insert 3A of the housing 3 with the first engagement means 5 of the cartridge holder 2. In the shown preferred embodiment of present invention, the proximal end of the cartridge holder 2 is further provided with an actuation means 70 designed to activate and lock a reset element (nut means 11) in an operational state (described below and shown in FIG. 3).

A cartridge 6 from which a number of doses of a medicinal product may be dispensed is provided in the cartridge holder 2. A piston 7 is retained in the cartridge 6.

A removable cap (not shown) can be releasably retained over the distal end of the cartridge holder 2. Preferably the cap comprises a clip which is snapped onto the cap. The cap can also be lacquered.

The distal end of the cartridge holder 2 is provided with suitable engaging means 8, such as a helical thread, bayonet or the like, for engagement with a suitable needle assembly (not shown) to enable medicament to be dispensed from the cartridge 6 and injected.

The medication delivery device 1 according to FIGS. 1a to 1c comprises a dosing mechanism which includes a piston rod 17. The piston rod 17 is of generally circular cross-section. A pressure foot 18 is located at the distal end of the piston rod 17. The pressure foot 18 is preferably made of two separate parts which are snapped together around a distal end portion of the piston rod 17. The pressure foot 18 is disposed to abut the proximal face of the piston 7. The piston rod 17 is movable in a distal direction by means of a drive device, thereby pushing the piston 7 to move axially within the cartridge 6 in the distal direction for medication delivery. A first thread 15 is formed at the distal end of the piston rod 17 (first threaded section 15). A second thread 16 is formed at the proximal end of the piston rod 17 (second threaded section 16). The first thread 15 and the second thread 16 are oppositely disposed. Preferably at least one of the first and second threads 15, 16 is a multi-start thread, most preferably both are two-start threads.

The drive device comprises a drive sleeve 19 which extends about the piston rod 17. The drive sleeve 19 is generally cylindrical. The drive sleeve 19 is provided at a distal end with a radially extending flange 20. A helical groove (thread) 21 extends along the internal surface of the drive sleeve 19. The second thread 16 of the piston rod 17 is adapted to work within the helical groove 21 of the drive sleeve 19.

A shoulder 22A and an extension 22B are formed at the proximal end of the drive sleeve 19. The extension 22B has reduced inner and outer diameters in comparison to the remainder of the drive sleeve 19. A proximal end of the extension 22B is provided with a radially outwardly directed flange 23.

A clutch 24 is disposed about the drive sleeve 19, between the drive sleeve 19 and an end stop 28 (described below). The clutch 24 is located adjacent the proximal end of the drive sleeve 19. The clutch 24 is generally cylindrical and is provided at the distal end with a series of circumferentially directed saw teeth 29. Each saw tooth comprises a longitudinally directed surface and an inclined surface. Towards the proximal end of the clutch 24 there is located a radially inwardly directed flange 30. The flange 30 of the clutch 24 is disposed between the shoulder 22A of the drive sleeve 19 and the radially outwardly directed flange 23 of the extension 22B. The proximal end of the clutch 24 is provided with a plurality of saw teeth 31. The clutch 24 is keyed to the drive sleeve 19 by way of splines (not shown) to prevent rotation between the clutch 24 and the drive sleeve 19. The clutch 24 is provided with a plurality of flexible arms 32 (not shown) that engage a plurality of splines on an interior surface of a dose dial sleeve 27 (described below).

A clutch plate 25 and a biasing means 26 are located between the distal end of the clutch 24 and the proximal face of the radially extending flange 20 of the drive sleeve 19. In the illustrated embodiment, the biasing means 26 is a spring. The proximal face of the clutch plate 25 is provided with a series of circumferentially directed saw teeth 33. The clutch plate 25 is secured against rotation with respect to the housing 3. The saw teeth 33 of the clutch plate 25 interact with the saw teeth 29 at the distal end of the clutch 24 during dose setting (described below).

An end stop 28 is disposed about the drive sleeve 19, between the drive sleeve 19 and the dose dial sleeve 27. The end stop 28 is secured against rotation with respect to the housing 3 and is free to move axially with respect to the housing 3. At the distal end of the end stop 28 a radially extending flange 34 is provided designed to engage with spline features (not shown) on an interior surface of the housing 3. In the illustrated embodiment, the external surface of the end stop 28 is provided with a helical groove (thread) that extends the full length of the end stop 28. The helical groove (thread) is engaged with a threaded insert 53 of the dose dial sleeve 27. An interior surface of the end stop 28 is provided with a number of spline features (not shown). The clutch plate 25 is engaged with these spline features and thereby secured against rotation with respect to the housing 3

A dose dial sleeve 27 is provided between the clutch 24 and the housing 3. A helical groove (thread) 41 is provided about an outer surface of the dose dial sleeve 27. The housing 3 is provided with a helical rib (thread) 42, adapted to be seated in the helical groove (thread) 41 of the dose dial sleeve 27. In the illustrated embodiment, the helical rib (thread) 42 is formed on an interior surface of an insert 43. The threaded insert 43 is secured against rotation and axial movement with respect to the housing 3. The helical rib 42 extends for a single sweep of the inner surface of the insert 43. A proximal end of the dose dial sleeve 27 is provided with an inwardly directed flange in the form of a number of radially extending members 45.

The housing 3 is further provided with a window 40 (not shown) through which a part of the outer surface of the dose dial sleeve 27 may be seen. A visual indication of the dose that may be dialed is provided on the outer surface of the dose dial sleeve 27. The window 40 conveniently only allows a visual indication of the dose currently dialed to be viewed. The window can be designed such that it allows an enlarged visual indication of the dose currently dialed to be viewed by acting as a magnifying lens. Preferably the window 40 is filled with a transparent polymer. Most preferably the window 40 is part of an insert of the housing 3 which is made by two component injection moulding, wherein a section with a dark polymer surrounds a section with a transparent polymer. The insert is immovably fixed to the housing, e.g. by means of an adhesive tape.

The threaded insert 43 of the housing 3 is provided with a series of radial stop features 55, 56 (not shown). A distal end of the dose dial sleeve 27 is provided with a plurality of stop features 44 (not shown) which abut the stop features 56 of the insert 43 to prevent the dose dial sleeve 27 from being wound out of the housing 3 any further when a maximum dose has been set.

A dose dial grip 46 is disposed about an outer surface of the proximal end of the dose dial sleeve 27. An outer diameter of the dose dial grip 46 preferably corresponds to the outer diameter of the housing 3. The dose dial grip 46 is secured to the dose dial sleeve 27 to prevent movement therebetween. The dose dial grip 46 is provided with central opening 47. An annular recess 48, located in the proximal end of the dose dial grip 46, extends around the opening 47.

A button 49 is provided at the proximal end of the medication delivery device 1. In the illustrated embodiment of instant invention, the button 49 is of generally 'T' section, with a stem 50. The button 49 is preferably free to rotate with respect to the housing 3. Preferably the button 49 contains a washer (not shown) made of a friction reducing material (e.g. a friction modified polymer material) in order to reduce the friction between the button and dose dial grip 46 during dose delivery. The stem 50 of the button 49 extends through the central opening 47 in the dose dial grip 46 and through the inner diameter of the extension 22B of the drive sleeve 19. The stem 50 of the button 49 is retained for limited axial movement in the drive sleeve 19 and the clutch 24. In the illustrated embodiment, a head 51 of the button 49 is generally circular. A skirt 52 depends from a periphery of the head 51. The skirt 52 is adapted to be seated in the annular recess 48 of the dose dial grip 46.

An internal surface at the distal end of the dose dial sleeve 27 is provided with a helical thread (not shown). In the illustrated embodiment, the helical thread of the dose dial sleeve 27 is provided on an internal surface of the threaded insert 53. The insert 53 is retained within the dose dial sleeve 27 by means of an end cap 54 secured to the distal end of the dose dial sleeve 27. The end cap 54 is secured against both rotational and axial movement with respect to the dose dial sleeve 27. The helical groove (thread) of the end stop 28 is engaged with the threaded insert 53 of the dose dial sleeve 27.

The medication delivery device 1 further comprises nut means 11 which is a reset element and which has a series of face teeth 12 on a distal surface and a threaded circular opening 13. The first thread 15 of the piston rod 17 extends through and is threadedly engaged with the threaded circular opening 13 of the nut means 11. The nut means 11 is prevented from axial movement in the distal and/or proximal direction with respect to the housing 3, e.g. in the proximal direction by means of a web 57 within the housing 3. The web 57 can be a separate component or can be formed as part of the housing 3. In the devices shown in FIGS. 1a to 1c the nut means 11 is in a operational state in which the nut means 11 is prevented from rotation with respect to the housing 3 by means of a locking means 9 and therefore prevents proximal movement of the piston rod 17 during dose setting and dose delivery.

In the illustrated embodiment, the medication delivery device 1 is further provided with a locking means 9. The locking means 9 is secured against rotational movement with respect to the housing 3, but the locking means 9 is free for limited axial movement with respect to the housing 3 when the housing 3 is engaged with or disengaged from the cartridge holder 2. The locking means 9 is provided on a proximal surface with a series of face teeth 10 for engaging the face teeth 12 of the nut means 11. A biasing means 14, in the form of a spring, is provided between the proximal face of the locking means 9 and a web 57 within the housing.

In the shown embodiments according to FIGS. 1a to 1c the cartridge holder 2 (medication receptacle) comprises actuation means 70 with ramps 71, the inclined surfaces of the ramps 71 interacting with inclined surfaces 72 of the locking means 9 when the cartridge holder 2 is being connected with the housing 3 (described later with respect to FIGS. 2a to 2c and 3). By this interaction the locking means 9 is moved into engagement with the nut means 11. The actuation means 70 thereby brings the nut means 11 in the operational state. This interaction will be described in detail below.

Accordingly, when the cartridge holder 2 (medication receptacle) is engaged with the distal end of the housing 3 the reset element 11 is in the operational state and when the cartridge holder 2 (medication receptacle) is disengaged from the distal end of the housing 3 the reset element 11 is in a resetting state In the operational state the reset element 11 is prevented from rotation with respect to the housing 3, the piston rod 17 being prevented from moving in a proximal direction, and in the resetting state the reset element 11 is allowed to rotate with respect to the housing 3, the medication delivery device being resettable by rotating the piston rod 17 in a second rotational direction and moving the piston rod 17 in the proximal direction.

Operation of the medication delivery device 1 in accordance with the present invention will now be described.

To dial a dose a user rotates the dose dial grip 46, thereby rotating the dose dial sleeve 27. During dose dialing the clutch 24 is engaged with the dose dial sleeve 27 via the saw teeth 31 at the proximal end of the clutch 24. As the clutch 24 is engaged with the rotating dose dial sleeve 27, the clutch 24 and the drive sleeve 19 rotate with the dose dial sleeve 27 because of the splined engagement of the clutch 24 and the drive sleeve 19.

Audible and tactile feedback of the dose being dialed is provided by the clutch plate 25 and the clutch 24. This feedback is provided by the saw teeth 29 of the clutch 24 gliding over the saw teeth 33 of the clutch plate 25 during the rotational movement of the clutch 24 with respect to the housing 3. During dose dialing, the clutch plate 25 is pushed axially towards the proximal end of the device by the biasing means 26, thus ensuring that the saw teeth 29 and 33 of clutch plate 25 and clutch 24 maintain contact. As the clutch plate 25 is secured against rotation by spline features on the interior surface of the end stop 28, which is secured against rotation with respect to the housing, the clutch 24 rotates relative to the clutch plate 25 during dose setting. Due to the profile of the saw teeth 29 and 33, preferably triangular, the saw teeth 29 of the clutch 24 are able to glide over the saw teeth 33 of the clutch plate 25 as the clutch 24 rotates. Preferably, the ratio of the angular spacing of the saw teeth 29 of the clutch 24 and the saw teeth 33 of the clutch plate 25 is such that each tooth pitch corresponds to a conventional unit dose, or the like.

The dose dial sleeve 27 is wound out of the housing 3 (rotational movement and axial movement in the proximal direction) when a dose to be dispensed is increased because of its engagement with (insert 43 of) the housing 3 via the threads 41, 42. The helical groove 41 of the dose dial sleeve 27 and the internal thread 21 of the drive sleeve 19 have the same lead. This allows the dose dial sleeve 27 to extend from the housing 3 and the drive sleeve 19 to climb along the second thread 16 of the piston rod 17 in the proximal direction at the same rate (rotational movement and axial movement in the proximal direction with respect to the housing 3 and with respect to the piston rod 17).

At the limit of travel, a radial stop (not shown) on the dose dial sleeve 27 engages with a stop feature 56 provided on the insert 43 of the housing 3 to prevent further movement. During dose setting rotation of the piston rod 17 is prevented due to the opposing directions of the first and second threads 15, 16 on the piston rod 17, the first thread 15 being engaged with the nut means 11 and the second thread 16 being engaged with the drive sleeve 19.

The end stop 28 which is prevented from rotating with respect to the housing 3, preferably by means of spline features (not shown), moves axially towards the proximal end of the housing 3 when the dose dial sleeve 27 rotates and moves in the proximal direction during dose setting. When a dose is set that can maximally be dispensed from the cartridge 6, the radially extending flange 34 abuts a radial stop means 60 formed on the piston rod 17, preventing the end stop 28 from further proximal axial movement and both the dose dial sleeve 27 and the drive sleeve 19 from rotating further in the direction for setting a larger dose.

Should a user inadvertently dial beyond the desired dosage, the medication delivery device allows the dosage to be dialed down without dispense of medicinal product from the cartridge 6. The dose dial grip 46 is counter rotated for this purpose. This causes the system to act in reverse. The reverse rotation of the clutch 24 causes the saw teeth 29 and 33 of the clutch 24 and the clutch plate 25 to ride over one another to create the clicks corresponding to dialed dose reduction. Preferably the saw teeth 29 and 33 are so disposed that the circumferential extent of each saw tooth corresponds to a unit dose.

FIG. 1a shows the medication delivery device in a state before a first dose has been set. FIG. 1b shows the medication delivery device 1 according to FIG. 1a in a state in which a dose has been set. The dose dial sleeve 27 is extending proximally from the housing 3.

When the desired dose has been dialed, the user may then dispense this dose by depressing the button 49. This displaces the clutch 24 axially towards the distal end of the device with respect to the dose dial sleeve 27, thereby decoupling the clutch 24 from the dose dial sleeve 27. However, the clutch 24 remains keyed in rotation to the drive sleeve 19. Therefore the decoupling of the clutch 24 results in a decoupling of the dose dial sleeve 27 and the drive sleeve 19 The dose dial sleeve 27 and associated dose dial grip 46 are free to rotate, guided by the helical rib 42 of the insert 43 located in the helical groove 41 of the dose dial sleeve 27. During dose delivery the dose dial sleeve 27 is wound back into the housing 3 in the distal direction.

The pressure of the user on the button 49 further results in an axial movement of the clutch 24 in the distal direction without rotation with respect to the housing 3. The axial movement of the clutch 24 moves the clutch plate 25 distally against the force of the biasing means 26 until the clutch plate 25 abuts a shoulder on the drive sleeve 19 and the clutch 24 and clutch plate 25 are engaged such that relative rotation between the clutch 24 and the clutch plate 25 is prevented, thus preventing rotation of the clutch 24 and the drive sleeve 19 with respect to the housing 3 during dose delivery. As the clutch plate 25 is splined to the end stop 28 to prevent rotation of the clutch plate 25 with respect to the housing 3, the clutch plate 25, the clutch 24 and the drive sleeve 19 travel together distally but do not rotate.

The axial movement of the clutch 24 causes the drive sleeve 19 to move axially in the distal direction. The distal longitudinal axial movement of the drive sleeve 19 further causes (by means of the internal thread 21 of the drive sleeve 19 and the second thread 16 of the piston rod 17) the piston rod 17 (first threaded section 15) to rotate and thus to wind through the opening 13 in the nut means 11, thereby to advance the piston 17 in the cartridge 6.

Once the dialed dose has been dispensed, the dose dial sleeve 27 is prevented from further rotation by a plurality of rotational stop features (not shown) extending from the dose dial grip 46 engaging with stop features 55 located on the insert 43 of the housing 3. In the illustrated embodiment, the rotational stop features extend axially from the dose dial grip 46 and have an inclined end surface. The zero position is determined by the abutment of one of the axially extending edges of the rotational stop features (not shown) with a corresponding stop 55 on the insert 43.

The rotational movement of the dose dial sleeve 27 during dose delivery causes the end stop 28 to move axially in a distal direction back to its initial position within the housing 3.

FIG. 1c shows the medication delivery device according to FIGS. 1a and 1b after a dose has been dispensed. The piston rod 17 and the piston 7 in the cartridge 6 have been advanced in the distal direction. The dose dial sleeve 27 and the end stop 28 are in their original position with respect to the housing 3.

When the final dose has been dispensed, the spent cartridge 6 may be removed and disposed of. To remove the cartridge 6, the cartridge holder 2 is disengaged from the housing 3 by disengaging the first and second engagement means 5, 4. Once the cartridge holder 2 is disengaged from the housing 3, the spent cartridge 6 can be removed from the cartridge holder 2 and a new cartridge 6 can be placed in the cartridge holder 2.

For reusing the medication delivery device 1 it has to be reset by moving the piston rod 17 proximally into its initial position. As long as the nut means 11 is in the operational state, the proximal movement of the piston rod 17 is prevented due to the opposing directions of the first and second threads 15, 16 on the piston rod 17, the first thread 15 being engaged with the non-rotatable nut means 11 and the second thread 16 being engaged with the drive sleeve 19 and due to the clutch 24 which couples the drive sleeve 19 with the dose dial sleeve 27 and therefore indirectly to the thread 42 of the housing, the clutch 24 thereby forming part of stop means which prevent proximal movement of the piston rod 17 in the operational state.

Therefore the nut means 11 has to be brought into the resetting state, in which it is allowed to rotate with respect to the housing 3 so that the piston rod 17 can be moved in the proximal direction.

Disengagement of the cartridge holder 2 from the housing 3 causes the locking means 9, under the force of the biasing means 14, to disengage from the nut means 11. The locking means 9 then does not prevent rotation of the nut means 11 anymore. The nut means 11 is thus not in the operational state anymore, it is in the resetting state. This allows the nut means 11 to rotate freely and therefore the piston rod 17 to be wound back up in the proximal direction.

In order to attach the cartridge holder 2 containing the new cartridge 6 on the housing 3, the piston rod 17 has to be moved axially in the proximal direction. This proximal movement may be caused by the piston 7 of the cartridge 6 abutting the end of the piston rod 17 and being moved proximally with respect to the housing 3 when the cartridge holder 2 with the cartridge 6 is moved towards the housing 3 by the user. Alternatively the user may push the piston rod 17 in the proximal direction e.g. by means of a finger and then attach the cartridge holder 2 with cartridge 6 to the housing 3. As the nut means 11 (which is threadedly engaged with the piston rod 17) is free to rotate with respect to the housing 3 in the resetting state the piston rod 17 is free to rotate and translate proximally until the locking means 9 and the nut means 11 engage. The pushing back of the piston rod 17 by means of the piston 7 of the new cartridge 6 which is pushed against the pressure foot 18 of the piston rod 17 has the advantage, that the pressure foot 18 of the piston rod 17 already abuts the piston 7 of the cartridge 6 when the device is reset. Therefore, the priming movement of the piston rod 17 (to remove air from the cartridge 6) can be very small and the loss of medication due to priming thus be kept to a minimum.

The cartridge holder 2 containing the new cartridge 6 is engaged with the housing 3 by moving the first and second engagement means 5, 4 into engagement. As the cartridge holder 2 is moved into engagement with the housing 3, the cartridge holder 2 first rotates and moves axially in a proximal direction, because the second engagement means 4 of the insert 3A of the housing 3 moves along the threaded section of the first engagement means 5 of the cartridge holder 2 until the second engagement means 4 reaches the annular groove section of the first engagement means 5. The further movement of the second engagement means 4 in this annular groove causes the cartridge holder 2 to rotate without moving axially with respect to the housing 3. The first and second engagement means 5, 4 are therefore movable into engagement by a movement of the cartridge holder 2 which ends in a rotational movement without axial movement of the actuation means 70 with respect to the housing 3. This further rotation of the cartridge holder 2 (without axial movement) causes the ramps 71 of the actuation means 70 to glide along the inclined surfaces 72 of the locking means 9. The locking means 9 is thereby moved axially in the proximal direction against the force of the biasing means 14 until the face teeth 10 of the locking means 9 are engaged with the face teeth 12 of the nut means 11, thereby bringing the nut means 11 (reset element) in the operational state. In this position the nut means 11 is secured against axial movement and against rotation. In this operational state the piston rod 17 is prevented from rotation in one rotational direction and from axial movement in the proximal direction with respect to the housing 3 but is allowed to rotate in the other rotational direction and move axially in the distal direction with respect to the housing 3 for medication delivery.

The pure rotational movement of the cartridge holder 2 and the actuation means 70 which moves the locking means 9 into engagement with the nut means 11 ends when snap-in features (not shown) of the cartridge holder 2 and the insert 3A of the housing 3 engage. In this position the actuation means 70 holds the nut means 11 in the operational state.

The rotational movement (without axial movement) of the cartridge holder 2 with respect to the housing 3 which moves the locking means 9 into engagement with the nut means 11 has the advantage of not building up any pressure on the piston 7 of the cartridge 6 before the medication delivery device 1 is used.

Thus the dosing mechanism of the medication delivery device 1 according to the present invention is reset into a zero (or no dose delivered) position as indicated in FIG. 1a.

FIGS. 2a to 2c show schematically an embodiment of an actuation means interacting with locking means in three different states according to one embodiment of the present invention.

FIG. 2a shows a locking means 9 and an actuation means 70 before an interaction takes place therebetween. In the shown embodiment the actuation means 70 is e.g. part of a medication receptacle (e.g. a cartridge holder 2) of the medication delivery device. In the shown embodiment the component of the medication delivery device comprising the actuation means 70 further comprises first engagement means 5 for engaging with second engagement means 4 which are preferably part of the housing of the medication delivery device or of an insert of the housing. The first and second engagement means 5, 4 are designed such that for moving the two components which comprise the engagement means 5, 4 (preferably the housing and the medication receptacle) into engagement, the two components are first rotated and moved axially with respect to each other (first step) and then only rotated without being moved axially with respect to each other (second step). The interaction between the actuation means 70 and the locking means 9 only takes place in this second step, when the two components (e.g. the medication receptacle and the housing) and therefore the actuation means 70 and the locking means 9 only rotate with respect to each other. The locking means 9 is preferably not rotatable with respect to the housing of the medication delivery device.

FIG. 2a shows the actuation means 70 and the locking means 9 during the first step, when both rotation (arrow 35) and axial movement (arrow 36) therebetween take place. During this step the second engagement means 4 moves along a first section of the first engagement means 5 which is represented by a thread 37. The distal end of the thread 37 merges into a second section of the first engagement means 5 which is represented by a part of annular groove 38. In the schematic drawing this annular groove 38 looks like a straight section because the drawing represents a view onto the outer surface of essentially cylindrical components.

The second engagement means 4 is at least one engaging element which engages with the thread 37 and the annular groove 38. The shown engaging element has the shape of a parallelogram.

In the shown embodiment the locking means 9 and the actuation means 70 have special shapes for interacting. The actuation means comprises ramps 71 with inclined surfaces for interacting with correspondingly inclined surfaces 39 of the locking means 9 which form triangular recesses 58.

In FIG. 2a the combined axial movement 36 and rotation 35 of the actuation means 70 with respect to the locking means 9 results in the actuation means 70 approaching the locking means 9 until the actuation means 70 abuts the locking means 9 in a position in which the ramps 71 are joined with the triangular recesses 58 of the locking means 9 as shown in FIG. 2b. In this position the second engagement means 4 has reached the point in which the thread 37 of the first engagement means 5 merges into the annular groove 38 of the first engagement means 5. The combined axial movement 36 and rotation 35 of the actuation means 70 with respect to the locking means 9 (first engagement step) now switches over into a rotation 35 only of the actuation means 70 with respect to the locking means 9 (second engagement step).

During this rotation the inclined surfaces of the ramps 71 and the recesses 58 glide along each other. This interaction of the actuation means 70 and the locking means 9 during the rotational movement without axial movement drives the locking means 9 (which is non-rotatable with respect to the (not shown) housing) axially in the proximal direction (arrow 59) as shown in FIG. 2c. By this axial movement of the locking means 9 (preferably against the force of a not shown biasing means) the locking means 9 is driven into engagement with a (not shown) reset element (e.g. a nut means), thereby bringing the reset element in a operational state in which it prevents proximal movement of the piston rod 17 during dose setting and medication delivery with the medication delivery device. The engagement of the locking means 9 and the reset element can be established e.g. by interlocking of (not shown) face teeth of the locking means 9 and the reset element.

FIG. 3 shows a cross-sectional enlarged view of a middle part of the embodiment according to FIGS. 1a to 1c showing the reset element of the medication delivery device in the operational state.

The cartridge holder 2 of the medication delivery device is attached to the housing 3 of the medication delivery device by first engagement means 5 being engaged with second engagement means 4 (not shown). The cartridge holder 2 comprises the first engagement means 5 and the insert 3A of the housing 3 comprises the second engagement means 4. A two-part pressure foot 18 is mounted on the distal end of the piston rod 17 and abuts the piston 7 of the medication cartridge 6.

According to this embodiment the cartridge holder 2 comprises actuation means 70 which comprise ramps 71 with inclined surfaces for interacting with correspondingly inclined surfaces 72 of locking means 9. The locking means 9 is engaged with a nut means 11 which is a reset element in the operational state for preventing the proximal movement of the piston rod 17. The tips of the ramps 71 of the actuation means 70 are pushed against the distal surface of the locking means 9, thereby holding the nut means 11 in the operational state. Face teeth 10 of the locking means 9 are engaged with face teeth 12 of the nut means 11. By this engagement of the nut means 11 with the locking means 9 rotation of the nut means 11 with respect to the housing 3 is prevented. The nut means 11 is in threaded engagement with the first thread 15 of the piston rod 17. By means of this threaded engagement and of the engagement of the (oppositely disposed) second thread 16 of the piston rod 17 with the (not shown) drive sleeve, movement of the piston rod 17 in the proximal direction is prevented as long as the nut element 11 is in the operational state. A biasing means 14 is provided to push the nut means 11 and the locking means 9 apart when the cartridge holder 2 is disconnected from the housing 3 (not shown).

FIG. 4 shows schematically a different embodiment of the medication delivery device according to the present invention with a different arrangement of actuation means and a reset element.

The actuation means 70 comprises ramps 71 and the medication receptacle 2 comprises first engagement means 5 with threaded sections 37 and an annular groove 38. The reset element 11 has inclined surfaces 39 for interaction with the ramps 71 of the actuation means 70. When the inclined surfaces of the ramps 71 and the reset element 11 abut and glide along one another during rotational movement of the actuation means 70 with respect to the housing 3 in the second engagement step, the reset element 11 is pushed against a locking means 9, face teeth 12 of the reset element 11 thereby engaging with face teeth 10 of the locking means 9. The locking means 9 of this embodiment is not necessarily a separate component. It can also be part of the housing 3.

FIG. 5 shows another embodiment of a medication delivery device according to the invention.

The medication delivery device 1 according to FIG. 5 comprises a cartridge holder 2 and a (exterior) housing 3. The distal end of the housing 3 is provided with an insert 3B designed to engage with the proximal end of the cartridge holder 2. The insert 3B is secured against rotation with respect to the housing 3 but is free to move axially with respect to the housing 3. The extent of axial movement of the insert 3B is limited by a retaining means 63 which is engaged with the housing 3 and secured against both axial and rotational movement with respect to the housing 3.

An inner surface of the insert 3B is provided with second engagement means 4. The second engagement means 4 could be any suitable means known by a person skilled in the art, such as a bayonet, helical thread, or the like. Preferably, the second engagement means 4 is a helical thread and corresponds to the first engagement means 5 at the proximal end of the cartridge holder 2, which is preferably also a helical thread.

In the shown embodiment of present invention, the proximal end of the cartridge holder 2 is further provided with an actuation means (not shown) designed to activate and lock a reset element (not shown) in an operational state.

A biasing means 64 is provided between the proximal face of the retaining means 63 and the distal face of the insert 3B. The biasing means 64 may be manufactured from any suitable flexible material known to a person skilled in the art, such as stainless steel, rubber, or the like, and may be in any suitable form, such as a spring, spacer, or the like. In the illustrated embodiment of instant invention, the biasing means 64 is a wave spring. The biasing means 64 is designed to ensure that the insert 3B does not abut the retaining means 63 when the cartridge holder 2 is not engaged with the housing 3.

The further components of this medication delivery device will not be described in detail, but are preferably similar to the components as described with reference to FIGS. 1a to 1c.

Operation of the drug delivery device in accordance with the present invention will now be described.

The dialing of a dose and the dispensing of a dose can e.g. work in a similar way as described with reference to FIGS. 1a to 1c.

When the final dose dispensed position is reached, the spent cartridge may be removed and disposed of. To remove the cartridge, the cartridge holder 2 is disengaged from the housing 3, preferably the cartridge holder 2 is unscrewed from the housing 3. Once the cartridge holder 2 is disengaged from the housing 3, the spent cartridge can be removed from the cartridge holder 2 and a new cartridge can be placed in the cartridge holder 2.

Disengagement of the cartridge holder 2 from the housing 3, causes the (not shown) reset element of the device to be moved out of its operational state, e.g. by a locking means under the force of a biasing means disengaging from the reset element. This for example allows the reset element to rotate freely and thus the piston rod to be moved in the proximal direction for resetting the device.

With the cartridge holder 2 removed, the insert 3B is free to move axially in a proximal direction away from the distal end of the housing 3 (away from the retaining means 63) for a limited distance by virtue of the force exerted by the biasing means 64.

In order to attach the cartridge holder 2 on the housing 3 the piston rod is moved axially in the proximal direction with respect to the housing 3. This proximal movement is caused by the piston of the new cartridge abutting the end of the piston rod and being moved proximally with respect to the housing 3 when the cartridge holder 2 with the cartridge is moved towards the housing 3. As the reset element is not yet in the operational state the piston rod is free to translate proximally until the reset element is in the operational state, e.g. until locking means and the reset element engage. The pushing back of the piston rod by means of the piston of the new cartridge which is pushed against the pressure foot of the piston rod has the advantage, that the pressure foot of the piston rod already abuts the piston of the cartridge when the device is reset. Therefore, the priming movement of the piston rod (to remove air from the cartridge) can be very small and the loss of medication due to priming thus be kept to a minimum.

The cartridge holder 2 containing the new cartridge is then engaged with the housing, preferably threadedly engaged. As the cartridge holder 2 is moved into engagement with the housing 3, the first engagement means 5 located at the proximal end of the cartridge holder 2 engages with the second engagement means of the insert 3B. The cartridge holder 2 is allowed to rotate and move axially in a proximal direction (first engagement step) until stop means 65 (e.g. an annular outer rim) located on the cartridge holder 2 abuts the retaining means 63 The stop means 65 prevent further axial movement of the cartridge holder 2 but allow the cartridge holder 2 to rotate (second engagement step). As the cartridge holder 2 rotates further, the insert 3B is moved axially, against the force of the biasing means 64, towards the distal end of the housing 3 and therefore towards the retaining means 63.

This pure rotation of the cartridge holder 2 additionally causes the activation means to bring the reset element into the operational state (not shown), e.g. by a locking means being moved axially in a proximal direction against the force of a biasing means until the face teeth of the locking means are engaged with face teeth of the reset element Thus the drive mechanism is reset into a zero (or no dose delivered) position The rotational movement (without axial movement) of the cartridge holder 2 which brings the reset element in the operational state has the advantage of not building up any pressure on the piston of the cartridge before the medication delivery device 1 is used for the first time after inserting a new cartridge.

REFERENCE NUMBERS 1 medication delivery device
2 cartridge holder
3 housing
3A insert of the housing
3B insert of the housing
4 second engagement means
5 first engagement means
6 cartridge
7 piston
8 engaging means
9 locking means
10 face teeth of locking means
11 reset element/nut means
12 face teeth of nut means
13 opening of nut means
14 biasing means
15 first thread of piston rod
16 second thread of piston rod
17 piston rod
18 pressure foot
19 drive sleeve
20 flange of drive sleeve
21 internal thread of drive sleeve
22A shoulder
22B extension
23 flange
24 clutch
25 clutch plate
26 biasing means
27 dose dial sleeve
28 end stop
29 saw teeth at distal end of clutch
30 flange of clutch
31 saw teeth at proximal end of clutch
32 flexible arms
33 saw teeth of clutch plate
34 flange at distal end of end stop
35 rotation
36 axial movement
37 thread
38 annular groove
39 inclined surfaces
40 window
41 outer helical thread of dose dial sleeve
43 thread of insert of the housing
44 stop features on dose dial sleeve
45 radially extending members
46 dose dial grip
47 central opening of dose dial grip
48 annular recess of dose dial grip
49 button
50 stem of button
51 head of button
52 skirt of button
53 threaded insert of dose dial sleeve
54 end cap
55 stop features on insert 43
56 stop features on insert 43
57 web
58 recesses
59 proximal direction 60 radial stop means on piston rod
63 retaining means
64 biasing means
65 stop means
70 actuation means
71 ramps
72 inclined surfaces

What is claimed is:

1. A dosing apparatus that generates audible and tactile feedback in a medication delivery device, the dosing apparatus comprising:
   a housing comprising a distal portion and a proximal portion;
   a piston rod axially moveable in the housing;
   a rotatable drive sleeve configured to move the piston rod axially during dose dispensing;
   a dose dial sleeve threadedly engaged to the housing, the dose dial sleeve comprising a dose dial grip disposed about an outer surface of a proximal end of the dose dial sleeve; and
   a clutch plate coaxially arranged with the dose dial sleeve, the clutch plate comprising a plurality of clutch plate teeth provided on a first surface of the clutch plate;
   wherein rotation of the dose dial sleeve causes a rotation of a first plurality of teeth to ride over the plurality of clutch plate teeth provided on the first surface of the clutch plate, so as to generate audible and tactile feedback when a dose of a medicament is being dialed by rotating the dose dial grip to increase or decrease a desired dosage.

2. The dosing apparatus of claim 1, wherein the first surface of the clutch plate comprises a proximal surface of the clutch plate.

3. The dosing apparatus of claim 1, wherein the clutch plate is movable in a proximal direction during dose dialing.

4. The dosing apparatus of claim 3, wherein the clutch plate moves in a distal direction during dose dispensing.

5. The dosing apparatus of claim 1, further comprising:
   a cylindrical threaded insert fixed to the proximal portion of the housing, wherein the dose dial sleeve is threadedly engaged with a helical rib provided by the cylindrical threaded insert.

6. The dosing apparatus of claim 5, further comprising:
   at least one radial stop provided along a surface of the cylindrical threaded insert.

7. The dosing apparatus of claim 6, further comprising:
   a distal end of the dose dial sleeve comprising at least one stop feature configured to abut the at least one radial stop provided along the surface of the cylindrical threaded insert, wherein the dose dial sleeve is prevented from being wound out of the housing any further when a maximum dose has been dialed.

8. The dosing apparatus of claim 1, further comprising:
   a helical thread extending along an internal surface of the drive sleeve.

9. The dosing apparatus of claim 8, further comprising:
   a thread provided by the piston rod, wherein the thread of the piston rod is adapted to work with the helical thread of the drive sleeve.

10. The dosing apparatus of claim 1, further comprising:
    a flange provided near a distal end of the drive sleeve.

11. The dosing apparatus of claim 1, further comprising:
    a cylindrical sleeve circumferentially arranged around the drive sleeve and the piston rod, wherein the cylindrical sleeve moves in a proximal direction during dose dialing.

12. The dosing apparatus of claim 11, wherein the cylindrical sleeve is movable in a distal direction during dose dispensing.

13. The dosing apparatus of claim 11 further comprising:
    a series of circumferentially directed saw teeth provided on a portion of the cylindrical sleeve, wherein the series of circumferentially directed saw teeth comprise the first plurality of teeth,
    wherein the rotation of the dose dial sleeve causes a rotation of the series of circumferentially directed saw teeth to ride over the plurality of clutch plate teeth provided by the clutch plate, so as to generate audible and tactile feedback when the dose of the medicament is being dialed by rotating the dose dial grip.

14. The dosing apparatus of claim 1 further comprising:
    a central opening defined by the dose dial grip, and
    an annular recess located in a proximal end of the dose dial grip and that extends around the central opening defined by the dial grip.

15. The dosing apparatus of claim 1 further comprising:
    a plurality of rotational stop features extending from the dose dial grip and configured to engage at least one stop feature located on a threaded insert of the housing.

16. The dosing apparatus of claim 15, wherein the plurality of rotational stop features extend axially from the dose dial grip and comprise an inclined end surface.

17. The dosing apparatus of claim 1 further comprising:
    a button provided near a proximal end of the dose dial grip, wherein the button comprises a "T" section button.

18. The dosing apparatus of claim 17, wherein the button comprises a rotatable button.

19. The dosing apparatus of claim 18, wherein the button further comprises a stem, and wherein the stem is configured to extend through a central opening in the dose dial grip.

20. The dosing apparatus of claim 17, wherein the button further comprises a circular head, and wherein a skirt depends from a periphery of the head.

21. The dosing apparatus of claim 20, wherein the skirt is adapted to be seated in an annular recess of the dose dial grip.

22. The dosing apparatus of claim 1, further comprising:
    a tubular member positioned within the dose dial sleeve and configured with a set of saw teeth, the set of saw teeth configured to engage a proximal end face of the clutch plate during dose dialing.

23. The dosing apparatus of claim 1, further comprising:
    an end stop, the end stop configured to prevent a setting of a dose which exceeds an amount of medication left in a medication receptacle contained within a cartridge holder connected to the dosing apparatus.

24. The dosing apparatus of claim 23, further comprising:
    a radially extending flange provided near a first portion of the end stop, the flange configured with a plurality of spline features.

25. The dosing apparatus of claim 23, wherein the end stop is movable in a proximal direction during dose dialing.

26. The dosing apparatus of claim 1, wherein the medication delivery device comprises a disposable device designed to dispense multiple selected doses of insulin.

27. The dosing apparatus of claim 1, further comprising:
    a shoulder and an extension formed at a first end of the drive sleeve, wherein the extension comprises a reduced outer diameter in comparison to the remainder of the drive sleeve.

28. The dosing apparatus of claim 1 further comprising:
a clutch, the clutch comprising a series of circumferentially directed saw teeth, each of the circumferentially directed saw teeth comprising a longitudinally directed surface and an inclined surface.

29. The dosing apparatus of claim 1, wherein the piston rod comprises a rotatable piston rod.

30. The dosing apparatus of claim 1,
wherein rotation of the dose dial sleeve in a first direction causes the rotation of the first plurality of teeth to ride over the plurality of clutch plate teeth provided on the first surface of the clutch plate, so as to generate audible and tactile feedback when the dose of the medicament is being dialed by rotating the dose dial grip to increase the desired dosage, and
wherein rotation of the dose dial sleeve in a second direction causes the rotation of the first plurality of teeth to ride over the plurality of clutch plate teeth provided on the first surface of the clutch plate, so as to generate audible and tactile feedback when the dose of the medicament is being dialed by rotating the dose dial grip to decrease the desired dosage.

31. The dosing apparatus of claim 30, wherein the clutch plate is rotationally fixed relative to the housing when rotating the dose dial grip in the first direction to increase the desired dosage and when rotating the dose dial grip in the second direction to decrease the desired dosage.

* * * * *

UNITED STATES PATENT AND TRADEMARK OFFICE
CERTIFICATE OF CORRECTION

PATENT NO. : 10,286,158 B2  
APPLICATION NO. : 15/175406  
DATED : May 14, 2019  
INVENTOR(S) : Michael Harms et al.

Page 1 of 1

It is certified that error appears in the above-identified patent and that said Letters Patent is hereby corrected as shown below:

On the Title Page

Column 1, item (72) (Inventors), delete "James Roberts Howarth" and insert -- James Robert Howarth --.

In the Specification

In Column 1, Line 7, delete "14/094,916" and insert -- 14/049,916 --.

Signed and Sealed this  
Twenty-seventh Day of August, 2019

Andrei Iancu  
*Director of the United States Patent and Trademark Office*